United States Patent [19]

Barrett et al.

[11] Patent Number: 5,468,480
[45] Date of Patent: Nov. 21, 1995

[54] PHARMACEUTICAL COMPOSITION OF PURIFIED CHYMOPAPAIN

[75] Inventors: Alan J. Barrett; David J. Buttle, both of Cambridgeshire, United Kingdom; Daniel H. Rich, Madison, Wis.

[73] Assignee: The Boots Company PLC, Nottingham, England

[21] Appl. No.: 302,369

[22] Filed: Sep. 8, 1994

Related U.S. Application Data

[62] Division of Ser. No. 768,325, Dec. 13, 1991, Pat. No. 5,380,656.

[30] Foreign Application Priority Data

Apr. 28, 1989 [GB] United Kingdom ............... 8909836

[51] Int. Cl.$^6$ ............................. A61K 38/48; C12N 9/50
[52] U.S. Cl. .......................... 424/94.65; 435/219
[58] Field of Search ........................ 435/212, 219; 424/94.65

[56] References Cited

U.S. PATENT DOCUMENTS

| | | | |
|---|---|---|---|
| 2,313,875 | 3/1943 | Jansen et al. | 195/66 |
| 3,320,131 | 5/1967 | Smith | 167/73 |
| 3,558,433 | 1/1971 | Stern | 195/66 |
| 4,374,926 | 2/1983 | Stern | 435/23 |
| 4,439,423 | 3/1984 | Smith | 424/94 |
| 4,719,108 | 1/1988 | Smith | 424/94.2 |
| 5,380,656 | 1/1995 | Barrett et al. | 435/219 |

FOREIGN PATENT DOCUMENTS

| | | |
|---|---|---|
| 270723 | 8/1989 | German Dem. Rep. |
| 1512491 | 6/1978 | United Kingdom. |
| WO84/00365 | 2/1984 | WIPO. |
| WO85/04417 | 10/1985 | WIPO. |

OTHER PUBLICATIONS

Rich et al., *Biochem. J.* (1986) 235, 731–734.
Luaces et al., *Biochem. J.* (1988) 250, 903–909.
Polgar, *Biochim. Biophys. Acta*, 658 (1981) 262–269.
Dubois et al., *Biol. Chem. Hoppe–Seyler* (1988) 369, 733–740.
Dubois et al., *Biol. Chem. Hoppe–Seyler* (1988) 369, 741–754.
Lynn, *Biochim. Biophys. Acta*, 569 (1979) 193–201.
Lynn et al., *Biochim. Biophys. Acta*, 581 (1979) 363–364.
Buttle et al., *Bicohem. J.* (1984) 223, 81–88.
Zucker et al., *Biochim. Biophys. Acta*, 828 (1985) 196–204.
Barrett et al., *Biochem. J. Letts.* (1985) 228, 527.
Buttle, Ph.D. Thesis (British Library) entitled "The Biochemical. Basis for the Use of Chymopapain in the Treatment of Sciatica" (1985).
Goodenough et al., *Bioscience Reports*, 6 (8), 759–766 (1986).
Goodenough et al., *Phytochemistry*, 26 (1), 75–79 (1987).
Baines et al., *J. Protein Chem.*, 1 (2), 119–139 (1982).
Korodi et al., *Biochemistry* (1986) 25, 6895–6900.
McKee et al., *Biochem. J.* (1986) 237, 105–110.
McKee et al., *Phytochemistry*, 25 (10), 2283–2287 (1986).
Schack et al., *Biochem. J.* (1984) 219, 727–733.
Robinson, *Biochemistry*, 14 (16), 3695–3700 (1975).
Blumberg et al., *Israel J. Chem.* (1969) 7, 125.
Kunimitsu et al., *Biochim. Biophys. Acta*, 139 (1967) 405–417.
Brocklehurst et al., *BJ Letters*, 228 (1985) 525–527.
Cockayne et al., *Current Concepts in Chemonucleolysis*, (Ed. J. Carl Sutton), 9–15 (1985).
Tsay et al., *Spine*, 9 (7), 764–771 (1984).
Lynn, *J. Chromatography*, 84 (1973) 423–425.
Joshi et al., *J. Chromatography*, 121 (1976) 65–71.
Burke et al., *Arch. Biochem. Biophys.*, 164, 30–36 (1974).
Sluyterman et al., *Biochim. Biophys. Acta*, 200 (1970) 593–595.
Stern, *Clin. Orthopaedic & Related Res.*, 67 (1969) 42–46.
Tsunoda et al., *J. Biol. Chem.*, 241 (20), 4610–4615 (1966).
Ebata et al., *J. Biol. Chem.*, 237 (4), 1086–1094 (1962).
Jansen et al., *J. Biol. Chem.* (1941) 137, 459–460.
Ebata et al., *Biochim. Biophys. Acta* (1966) 118, 201–203.
Schack, *Compt. Rend. Trav. Lab Carlsberg* (1967) 36, 67–83.
Johansen et al., *Compt. Rend. Trav. Lab Carlsberg* (1968) 36, 265–283.
Kunimitsu et al., *Methods Enzymol* (1970) 19, 244–252.
Clagett et al., *Soc. Exp. Biol. Med.* (1974) 145, 1250–1257.
Baines et al., *Biochem. Soc. Trans.* (1978) 6, 255–258.
Brocklehurst et al., *Biochem. J.* (1980) 189, 189–192.
Khan et al., *Biochim. Biophys. Acta* (1983) 760, 350–356.
Brocklehurst et al., *Biochem. J.* (1983) 213, 559–560.
Polgar, *Biochem. J.* (1984) 221, 555–556.
Brocklehurst et al., *Biochem. J.* (1984) 221, 553–554.
Brocklehurst et al., *Biochem. J.* (1984) 228, 525–527.
Solis–Mendiola et al., *Biochem. J.* (1989) 257, 183–186.
Jacquet et al., *Biol. Chem. Hoppe–Seyler*, 370, 425–434 (May 1989).
Buttle et al, *Biochem. J.* (Jul. 1989) 261, 469–476.
Jacquet. et al. *Biol. Chem. Hoppe–Seyler*, 370, 819–829 (Aug. 1989).
Ritonja et al., *FEBS Letters*, 258 (1), 109–112 (Nov. 1989).
Buttle et al., *FEBS Letters*, 260 (2), 195–197 (Jan. 1990).
Watson et al., *Biochem. J.* (Feb. 1990), 266, 75–81.
Buttle et al., *FEBS Letters*, 262 (1), 58–60 (Mar. 1990).
Buttle et al., *Biol. Chem. Hoppe–Seyler* (1990) 371, 1083–1088.
Smith, *J. Amer. Med. Assoc.* (1984) 187, 137–140.
Rowan et al., *Arch. Biochem. Biophys.* (1988) 26, 262–270.

(List continued on next page.)

Primary Examiner—Marian C. Knode
Assistant Examiner—Jon P. Weber
Attorney, Agent, or Firm—Nikaido, Marmelstein, Murray & Oram

[57] ABSTRACT

A pharmaceutical composition comprising purified chymopapain and a reducing agent is presented. The purified chymopapain in this composition has a specific activity against 1 mM of N-α-benzoyl-DL-arginine p-nitroanilide at 40° C. and pH 6.8 of between 3,000 and 4,500 units per mg, and contains less than 0.2% each of papaya proteinase III (PPIII), papain, and papaya proteinase IV (PPIV).

6 Claims, No Drawings

OTHER PUBLICATIONS

Mancini et al., *Immunochem.* (1965) 2, 235–254.
Heide et al., *Handbook of Experimental Immunology* (1978) vol. 1, 7.1–7.11, Blackwell, Oxford (Weir D. M. ed).
Kemeny et al., *J. Immunol. Methods* (1988) 108, 105–113.
Salih et al., *Biochem. J.* (1987) 247, 181–193.

Anastasi et al., *Biochem. J.* (1983) 211, 129–138.

R. Arnon et al., *Biochemistry*, vol. 7, No. 12, Dec. 1968, pp. 4196–4202 "Comparison between the antigenic structure of mutually related enzymes".

Buttle et al., *Brit. J. Radiol.* 57, 475–477 (1984).

PHARMACEUTICAL COMPOSITION OF PURIFIED CHYMOPAPAIN

This is a division of application Ser. No. 07/768,325, filed Dec. 13, 1991, now U.S. Pat. No. 5,380,656.

This invention relates to chymopapain, improved pharmaceutical compositions containing chymopapain and to methods of treating damaged, herniated or otherwise abnormal intervertebral mammalian spinal discs which comprise injecting into said discs a solution of the improved composition. The invention further relates to processes for preparing the chymopapain of the invention, to peptides and affinity chromatography matrices of use in such processes, and to monospecific antibody preparations raised against chymopapain.

Chymopapain is a cysteine proteinase present in the latex of the paw-paw (Carica papaya) plant. It has been found to be of clinical use, particularly for the treatment of prolapsed or herniated discs or sciatica in a process known as "chemonucleolysis", Smith, L. (1964), J. Amer. Med. Assoc. 187, 137–140.

Purification and characterisation of chymopapain was first attempted by Jansen and Balls (1941), J. Biol. Chem., 137, 405–417 who used acid precipitation and a salting-out procedure to prepare the enzyme. More recently, purification methods based on ion-exchange chromatography have been employed. Thus, for example, GB2098997 (Smith Laboratories Inc.) and GB215682(Simmons) both describe the use of cation-exchange resins to separate chymopapain from other known cysteine proteinases and these processes have both been used to prepare chymopapain on an industrial scale. However, the resulting material is found to be of relatively low specific activity compared to the chymopapain prepared by Buttle and Barrett (1984), Biochem. J., 223, 81–88 using a multi-stage process on a small scale incorporating inter alia a cation-exchange chromatography step. Whilst this material was of high specific activity it was obtained in only very low yields and the process is not suitable for application on a commercial scale. Buttle et al., Biochem. J. (July 1989) 261, 469–476, have now found that this material is contaminated with a recently isolated and characterised proteinase, papaya proteinase IV, which co-elutes with chymopapain from cation-exchange resins. Cation-exchange chromatography is unable to separate chymopapain from papaya proteinase IV to an extent which could be of use in the preparation of chymopapain substantially free of contamination with papaya proteinase IV.

The literature also contains references to methods employing affinity chromatography steps. Polgar (1981), Biochim. Biophys. Acta, 658, 262–269, describes the purification of chymopapain using, amongst a number of other techniques, affinity chromatography on an agarose-mercurial column and Dubois et al., Biol. Chem. Hoppe-Seyler (1988), 369, 733–740, have reported separation of cysteine proteinases from Carica papaya latex using a similar technique. This type of affinity chromatography relies on the interaction between mercuric ligands bound to an inert matrix and the thiol groups of the proteins exposed thereto. Thus, proteins other than chymopapain, particularly other cysteine proteinases such as papaya proteinase IV, can bind to such columns and can subsequently be co-eluted with chymopapain.

Recently, scientific papers have described the use of affinity chromatography using immobilised peptide derivatives to purify specific proteinases such as human cathepsin B (Rich et al., 1986, Biochem. J. 235, 731–4) and histolysin from Entamoeba histolytica (Luaces & Barrett, 1988, Biochem. J. 250, 903–909). This approach had not hitherto been applied to procedures for purifying chymopapain and the need for an improved process for purifying chymopapain, suitable for use on an industrial scale, remains apparent.

Certain synthetic peptide derivatives which are inhibitors of the serine proteinase chymotrypsin have been described in WO84/00365.

The inventors have now discovered a novel process to purify and isolate highly active chymopapain free from contaminants and, in particular, free from the other cysteine proteinases present in papaya latex, including papaya proteinase IV.

The present invention provides chymopapain which is substantially pure and which contains a high proportion of the active form of the enzyme.

The chymopapain according to the present invention is substantially free of the immunologically distinct proteinases found in papaya latex, namely papain, papaya proteinase III (PPIII), both described by Buttle & Barrett (1984), Biochem. J., 223, 81–88, and in particular the recently discovered papaya proteinase IV (PPIV). "Substantially pure" as used herein may therefore be further defined as "substantially immunologically pure" and refers to the absence of any substantial cross-reaction between chymopapain according to the invention and specific antibodies raised against pure PPIV, isolated and characterised by Buttle et al., Biochem. J. (July 1989) 261, 469–476 and described in brief hereinafter, as well as the absence of any substantial cross-reaction with specific antibodies raised against papain and PPIII as previously described by Buttle and Barrett (1984), loc. cit. It is of particular note that the so-called "pure" chymopapain prepared by the method of Buttle and Barrett has been found to contain substantial amounts (about 14%) of PPIV and hence the anti-chymopapain antibody preparation originally raised by them has specificity for both purified chymopapain according to the invention and for purified PPIV. The chymopapain according to the invention contains less than 0.2%, preferably not more than 0.1% each of PPIV, PPIII and papain.

Cross-reaction between antigen and antibody may be determined by conventional techniques well known in the art. Such techniques include, for example, fused rocket immunoelectrophoresis and double immunodiffusion (described by Buttle and Barrett (1984), loc. cit.), single radial immunoassay, radioimmunoassay (RIA) and enzyme-linked immunosorbent assay (ELISA).

The amount of active enzyme present in any enzyme preparation is generally indicated in terms of its specific activity against a specified substrate under specified assay conditions. The expression "specific activity against BAPNA" as used herein denotes proteinase activity in picomole of p-nitroaniline formed per second per mg dry weight of the product (pmol/sec/mg) when assayed with the/synthetic substrate N-α-benzoyl-DL-arginine p-nitroanilide (BAPNA) under standard assay conditions. The standard assay conditions used for known pharmaceutical preparations of chymopapain are described in detail hereinafter as "BAPNA Assay Method No. 1" or "Smith assay" and the specific activities derived therefrom are referred to in terms of specific activity against BAPNA (1 mM) at 37° C. and pH 6.0. Chymopapain according to the invention is defined as having a specific activity against BAPNA (1 mM) at 37° C. and pH 6.0 of between 800 and 1700 units per mg, preferably of between 1000 and 1700 units per mg, for example 1200 to 1500 units per mg, when assayed at 37° C. and pH 6.0. In a preferred aspect the invention provides chymopapain having a specific activity against BAPNA (1 mM) at 37° C. and pH 6.0 of at least 1300 units per mg.

Whilst proteinase activity is very widely defined throughout the extensive literature relating to chymopapain and other cysteine proteinases in terms of the release of p-nitroaniline from the synthetic substrate BAPNA, problems can be encountered when a direct comparison between quoted specific activity figures is made. The precise values arrived at depend on a number of factors particularly relating to the precise conditions, for example the pH, temperature, buffer composition and substrate concentration used in the assay. The chymopapain prepared by Buttle and Barrett (1984), loc. cit. was quoted in their paper to have a specific activity against BAPNA of 0.154 µmol/min/mg which equates to 2567 pmol/sec/mg. However, the assay conditions used by Buttle and Barrett differed from those used for known pharmaceutical grades of chymopapain and the specific activities cannot be directly compared.

Since the material prepared by Buttle and Barrett was believed to be the chymopapain preparation having the highest specific activity hitherto reported, initial work relating to the present invention was carried out using the assay conditions specified in their paper. This method is referred to herein as BAPNA Assay Method No. 2 and the specific activities derived therefrom are referred to in terms of specific activity against BAPNA (2.5 mM) at 40° C. and pH 6.8 to make it clear that the assay conditions differ from those used for pharmaceutical preparations of chymopapain. The results obtained using this assay have been shown to be two to three times higher than those obtained using the conventional pharmaceutical BAPNA Assay Method No. 1 although it would be scientifically incorrect to apply a simple conversion factor to convert results obtained from one assay method to those of another. Nevertheless, early work relating to this invention has shown that the specific activity against BAPNA (2.5 mM) at 40° C. and pH 6.8 of pure chymopapain according to the invention may be defined as between 3000 and 4500 units per mg, for example 3500 to 4500 units per mg.

The inventors of the present invention, in work which has recently been published (July 1989, loc. cit) and which is described in brief hereinafter, have purified and characterised a previously unknown contaminant of chymopapain prepared by the prior art methods, namely papaya proteinase IV (PPIV). Whilst PPIV is inactive against BAPNA it does have proteinase activity against azocasein. Furthermore, it was found that PPIV activity against azocasein is not substantially inhibited by concentrations of chicken cystatin up to 1 µM. The activity against azocasein of chymopapain according to the invention is at least 95% inhibited by these concentrations of chicken cystatin. The expression "activity against azocasein" as used herein denotes proteinase activity in terms of the amount of trichloroacetic acid-soluble peptides formed per unit time per unit dry weight of the product when assayed with the derivatised protein substrate azocasein under the standard assay conditions described hereinafter. Preferably the chymopapain according to the invention has an activity against azocasein which is at least 97%, more particularly 98 to 100% inhibited by concentrations of chicken cystatin up to 1 µM.

The applicants believe i that the chymopapain according to the present invention is substantially pure chymopapain prepared for he first time without contaminating proteins and containing a high proportion of the active form of the enzyme. This breakthrough could only be achieved following the discovery that a contaminating protein had hitherto been co-purified with chymopapain for example on ion-exchange and known affinity columns. Further work ed to the isolation and characterisation of the contaminant as PPIV. The process used to prepare PPIV was not applicable to the preparation of pure chymopapain but the preparation of PPIV did provide two important parameters by which pure chymopapain could be characterised, namely 1) the absence of cross-reactivity of pure chymopapain with PPIV-specific antibodies and 2) the differential activity of pure chymopapain and PPIv against azocasein in the presence of chicken cystatin. These two characteristics were essential tools required for the development of processes suitable for purifying chymopapain.

It is readily apparent that chymopapain according to the invention will be the chymopapain of choice in almost all envisaged fields of activity. Pure enzyme preparations are of vital importance to those who attempt to fully characterise enzymes, for example in terms of their catalytic specificity and structure.

Accordingly a further aspect of the present invention provides a composition which comprises chymopapain according to the invention. The composition is substantially free of PPIV. The chymopapain has a specific activity against BAPNA (1 mM) at 37° C. and pH 6.0 of between 800 and 1700 units per mg. Compositions may be in the form of discrete units of an appropriate weight, for example in the form of aliquots of chymopapain sealed under anhydrous conditions such as in evacuated vials or ampoules. Such compositions may further comprise a reducing agent such as dithiothreitol, cysteine free base or an acid addition salt thereof, to substantially prevent inactivation of the enzyme by oxidation. Alternatively, compositions may further comprise a reversible cysteine proteinase inhibitor provided in the form of a salt such as, for example, sodium tetrathionate or mercuric chloride. These reversible inhibitors block the active site of the enzyme, thereby preventing its inactivation by oxidation, until displaced by, for example, a reducing agent which reactivates the enzyme. Other conventional additives, for example preservatives such as sodium bisulphite, chelating agents such as EDTA, and carriers such as sodium chloride, may be added if desired.

The use of a pure enzyme preparation is particularly important in the clinical applications of chymopapain, for example chemonucleolysis, where it has been reported that allergic reactions to such treatment may arise in as many as 3% of the patients treated. Powdered papaya extract is widely used in the food industry and it is thought that many of the allergic reactions to chemonucleolysis are due to pre-sensitisation with such preparations. However, it is well known that the injection of foreign protein antigens into mammals always carries with it a risk of anaphylactic shock. It will be in accordance with sound medical practice to use the purest and most active form of any such protein which is available to obtain optimal benefits of the procedure as well as minimising the risk of allergic reactions.

Thus a preferred aspect of the invention provides a pharmaceutical composition which comprises chymopapain according to the invention. The composition is substantially free of PPIV. The chymopapain has a specific activity against BAPNA (1 mM) at 37° C. and pH 6.0 of between 800 and 1700 units per mg. Pharmaceutical compositions preferably further comprise a pharmaceutically acceptable non-toxic reducing agent such as a cysteine free base or an acid addition salt thereof, for example, L-cysteine hydrochloride monohydrate. Generally the reducing agent is present in an amount of about 0.5 to 3 mg per 4000 units chymopapain, constituting for example 15 to 90% by weight of chymopapain. However pharmaceutical compositions according to the invention may further comprise any conventional pharmaceutically acceptable diluent, excipient or carrier, for example preservatives such as sodium bisulphite, chelating agents such as EDTA, and carriers such as sodium chloride, may be added if desired.

Pharmaceutical compositions containing chymopapain according to the invention may be of use in ophthalmology, for example in the treatment of eye lesions or for debridement of eschar tissues of, for example, burns, ulcers, pressure necroses, bed sores and other wounds in which devitalised tissues are present. Such compositions are generally provided in a form suitable for topical application, for example sterile solutions, gels, suspensions or ointments which may be applied directly to the wound or may be applied via a wound dressing impregnated with the composition.

Preferably the chymopapain according to the invention is formulated for orthopaedic use. Such pharmaceutical compositions may be conveniently prepared in unit dosage form for parenteral administration, for example in the form of a sterile, pyrogen-free solution or suspension in a suitable carrier or in a concentrated form suitable for reconstitution prior to use. Dosage unit forms suitable for use in dissolving or treating the nucleus pulposus of an abnormal or damaged intervertebral disc by injection therein may consist of between 500 and 5,000 BAPNA units (assayed with 1 mM BAPNA at 37° C. and pH 6.0) of chymopapain according to the invention and a reducing agent such as sodium cysteinate hydrochloride packaged in an evacuated vial. A preferred dosage unit form comprises nominally 2,000 or 4,000 BAPNA units mM BAPNA, 37° C., pH 6.0) of chymopapain. A dosage unit form may broadly consist of, for example, 2 to 5 mg, preferably 2.5 to 3.5 mg of chymopapain and 0.2 to 3 mg, preferably 1.0 to 2.0 mg of sodium cysteinate hydrochloride packaged in an evacuated container, optionally in admixture with a suitable carrier such as sodium chloride.

In experiments described hereinafter 26 individual serum samples were found to have naturally acquired IgE antibodies against a commercially available chymopapain preparation Chymodiactin$^R$, produced in accordance with the process described in GB 2098997. It has been experimentally demonstrated herein that these sera contain IgE antibodies to chymopapain according to the invention and to three other cysteine proteinases found in papaya latex, namely papain, PPIII and PPIV. However, averaged IgE levels for chymopapain, PPIII and PPIV have shown that PPIII and PPIV together account for nearly 75% of the IgE detected. These results clearly indicate that these proteins have substantial immunogenic character and may represent a major proportion of the antigenic determinants contained in hitherto available forms of chymopapain and pose a surprisingly large potential antigenic hazard. The pharmaceutical compositions of the invention thus have substantial advantages over the prior art compositions.

The present invention also relates to a method of treating by chemonucleolysis a damaged, herniated or otherwise abnormal intervertebral mammalian spinal disc which comprises injecting into said disc a pharmaceutically acceptable solution of chymopapain according to the invention in an amount sufficient to selectively dissolve portions of said disc.

The invention further relates to a method of treating an abnormal spinal disc in a mammalian subject which comprises:

i) inserting a needle into said disc;

ii) confirming the placement of said needle by means of X-ray; and iii) injecting into said disc a pharmaceutically acceptable solution of chymopapain according to the invention in an amount sufficient to selectively dissolve portions of said disc.

The present invention also provides a process for purifying chymopapain which comprises:

a) incubating an aqueous solution of crude chymopapain with an active site directed affinity chromatography matrix comprising a support matrix covalently coupled, optionally via a spacer arm, to the N-terminal of a reversible chymopapain inhibitory peptide such that said peptide binds to the active site of a chymoapain molecule; and b) eluting the chymopapain with a suitable eluent.

The crude chymopapain used as the starting material for the purification of the chymopapain according to the invention may be an extract of fresh papaya latex, a solution obtained from a commercially available preparation of spray-dried latex, papain concentrate or partially purified chymopapain, or may be a solution of a commercial preparation of so-called "pure" chymopapain. However, it will be appreciated by those skilled in the art that relatively complete extracts of papaya such as papaya latex will contain very substantial amounts of other naturally occurring components which it is desirable to remove. Preferably a substantial proportion of such components is removed before the crude chymopapain solution is incubated with the affinity chromatography matrix for example by filtration or centrifugation to remove insoluble material. However, we have found an acid precipitation step, during which a substantial fraction of impurities is precipitated, to be of particular advantage.

Acid precipitation procedures in which the pH of an aqueous solution of crude chymopapain is reduced to as low as pH2, allowed to stand and then the chymopapain solution separated out, have been used to purify chymopapain for almost 50 years. Surprisingly the applicant has now shown that the precise pH used in such procedures critically influences the contamination of the resultant chymopapain solution with PPIV. Careful monitoring and control of this procedure, hitherto thought to be a crude preliminary step in chymopapain purification, has been found to dramatically reduce contamination with PPIV, the protein which has now been found to copurify with chymopapain using conventional techniques. Accordingly, the invention provides a process for purifying chymopapain which comprises:

1. precipitating an aqueous mixture containing crude chymopapain at a pH of 1.2 to 1.8;

2. separating an aqueous solution of crude chymopapain from said mixture; and 3. neutralising and optionally de-salting said solution of crude chymopapain.

It is preferred to remove any remaining protein contaminants from the preparation by including at least one conventional cation-exchange chromatography step during the purification process, for example, as described by Buttle and Barrett, 1984, loc. cit. It is particularly preferred to employ high performance chromatography for example FPLC$^R$ on a cation-exchange resin such as those sold under the trade names Mono-S or S-Sepharose$^R$ HP (Pharmacia), as the final step.

A particularly preferred aspect of the invention provides a process for purifying chymopapain which comprises:

i) precipitating an aqueous mixture containing crude chymopapain at a pH of less than 2.0;

ii) separating an aqueous solution of crude chymopapain from said mixture;

iii) neutralising and optionally de-salting said solution of crude chymopapain;

iv) incubating the solution obtained from step (iii) with an active site directed affinity chromatography matrix comprising a support matrix covalently coupled, optionally via a spacer arm, to the N-terminal of a reversible chymopapain inhibitory peptide such that said peptide binds to the active site of a chymopapain molecule; and v) eluting the chymopapain with a suitable eluent.

It will be apparent to the skilled person that the preferred cation-exchange chromatography step may alternatively or additionally be employed immediately before or after the affinity chromatography step as desired.

The aqueous mixture containing crude chymopapain may comprise for example fresh papaya latex, spray-dried papaya latex or papain concentrate (for example, spray-dried latex commercially available from Powell & Scholefield, UK or from Siebels, USA) suspended in water or in an aqueous buffer such as phosphate or acetate buffer. Preferably insoluble material is removed in conventional manner, for example by filtration or centrifugation, prior to acid precipitation of the mixture. The mixture may be acidified by the gradual addition of organic or inorganic acid, preferably an aqueous inorganic acid such as hydrochloric acid, to reduce the pH of the mixture to between 1.0 and 2.0, preferably 1.2 to 1.8, more particularly to a pH of about 1.5. Precipitated material may be removed in conventional manner, for example by filtration or centrifugation. The resultant acidic crude chymopapain solution has been found to be depleted in PPIV, papain and, to a lesser extent, PPIII.

Before subjecting the acidic crude chymopapain solution to any further chromatography steps, persons skilled in the art will appreciate the need to neutralise the solution with an alkaline reagent such as aqueous sodium hydroxide and preferably to remove excess salts from the solution in conventional manner, for example by gel filtration or dialysis. Any further precipitated material may be removed by filtration or centrifugation.

It is well known in the art of cysteine proteinases that the activity of such enzymes may be appreciably enhanced by activation with a reducing agent such as dithiothreitol or cysteine and by the removal of traces of heavy metals such as mercury with a chelating agent such as EDTA or a chelating resin such as that sold under the trade name Chelex (Bio-Rad, UK). Such measures optimise the presence of free thiol groups which are known to be essential features of the active sites of cysteine proteinases and are required for activity. Preferably the removal of heavy metals is achieved by dialysis against a buffer containing EDTA. Alternatively, where a cation-exchange chromatography step is employed heavy metals may be removed by activating the chymopapain with a reducing agent whilst it is bound to the cation-exchange column and subsequently washing the column.

Advantageously the crude chymopapain solution obtained after neutralisation is treated with a reducing agent such as cysteine, to ensure maximal exposure of active sites, and diluted to a suitable protein content, for example 30 mg/ml. The neutralised crude chymopapain solution is then incubated with an active site directed affinity chromatograph matrix such that chymopapain is specifically bound, via the active site, to an inhibitory peptide bound thereto. Chymopapain solution may be applied to a column of affinity chromatography matrix at a rate of, for example, 35–40 ml/hr/cm$^2$. Approximately 1–4 g chymopapain may be bound per liter affinity chromatography matrix.

The affinity chromatography matrix comprises a support matrix such as a gel or membrane matrix to which an inhibitory peptide is covalently coupled and thereby immobilised. Preferably the support matrix is an agarose gel such as those sold under the trade name Sepharose$^R$ (Pharmacia) although derivatised cellulosic membrane matrices such as those sold under the trade name Zeta (Anachem) may also be utilised. The N-terminal of the peptide may be bound to the support matrix either directly or indirectly via a spacer arm, for example a nine carbon atom spacer arm such as that provided by a preferred gel matrix sold under the trade name ECH Sepharose$^R$ 4B (Pharmacia). Coupling between the free carboxy groups of this gel matrix and the free amino groups of the inhibitory peptide, resulting in peptide bond formation, may be achieved in conventional manner, for example by acid catalysed condensation promoted with a water soluble carbodiimide such as N-ethyl-N'-(3-dimethylaminopropyl)carbodiimide hydrochloride (EDC). Generally coupling is achieved by gently agitating the gel matrix and a solution of the inhibitory peptide together in the presence of EDC, for example at room temperature for 24 hours. A suitable coupling ratio of peptide to gel matrix is, for example, 3–4 g peptide per liter of gel.

The affinity chromatography matrix may be pre-packed into a column prior to use. However, where the chromatography matrix used is a gel matrix it is also possible to utilise a batch-wise incubation step and then, if desired, to pack the matrix into a column for subsequent elution of the enzyme. Preferably the matrix is washed well with aqueous buffer before use to remove traces of unbound peptide and condensation catalyst. For production use a column of affinity chromatography matrix should preferably withstand sanitation in situ, for example with aqueous ethanol and thus be reusable.

Reversible chymopapain inhibitory peptides are peptides which, when immobilised on a support matrix, are able to bind to the active site of chymopapain more strongly than to the active sites of other cysteine proteinases found in crude chymopapain preparations, particularly PPIV, but which can subsequently be displaced therefrom. In a preferred group of inhibitory peptides the C-terminal amino acid comprises an aldehyde derivative such as semicarbazone, methoxyimine or oxime of phenylalanine or a phenylalanine analogue. More particularly the C-terminal amino acid may be a phenylalanine derivative such as D or L-phenylalanine semicarbazone (PheSc), methoxyimine (PheMo) or oxime (PheOx) or a phenylalanine analogue derivative such as D or L-alanine semicarbazone (AlaSc), D or L-cyclohexylalanine semicarbazone (ChaSc) or D or L-leucine semicarbazone (LeuSc). The following C-terminal dipeptides have been found to be advantageous chymopapain inhibitory peptides, namely L-Kta-L-PheSc, L-Ala-D-PheSc, L-Phe-D-PheSc, L-Phe-L-PheSc, L-Phe-L-PheMo, L-Phe-L-PheOx, L-Tyr-L-PheSc, L-Ala-L-ChaSc and L-Ala-L-LeuSc. The dipeptide L-Phe-L-PheSc has been described by Luaces and Barrett (1988), 250, 903–909. Particularly preferred peptides are dipeptides especially L-Ala-L-PheSc, L-Ala-D-PheSc and L-Phe-D-PheSc. The novel inhibitory peptides per se and novel affinity chromatography matrices containing these peptides form further aspects of the present invention.

Prior to elution of chymopapain from the affinity chromatography matrix it is preferred to wash the matrix to remove non-specifically bound material, for example with an aqueous buffer such as citrate or acetate buffer of pH 4 to 5. It has been found to be particularly advantageous to add reagents to the washing buffer and to the elution buffer which reduce hydrophobic interactions and other non-specific binding reactions between the matrix and the crude chymopapain components. Such reagents include for example EDTA, isopropanol and ethanediol.

The chymopapain may then be eluted from the matrix with a suitable eluent. Suitable eluents disrupt the binding between the immobilised inhibitory peptide and the chymopapain bound thereto, either by reducing the affinity of the active site for the inhibitory peptide or by selectively displacing the peptide from the active site. The affinity of chymopapain for the inhibitory peptide may be reduced, for example, by altering the characteristics of the active site with a denaturing agent such as isopropanol or with an eluent having a pH above or below the active pH range of chymopapain. However, it will be appreciated by those skilled in the art that such eluents must be such that irreversible inactivation of the eluted enzyme does not occur. Alternatively, chymopapain may be selectively displaced from the immobilised inhibitory peptide by an eluent comprising an excess of a component which binds tightly to the inhibitory peptide, for example another cysteine proteinase.

However, in a preferred aspect of the present invention the eluent comprises a reversible cysteine proteinase inhibitor which competitively binds to the active site of chymopapain and thus displaces it from the immobilised inhibitory peptide. Conventional inhibitors include, for example, low molecular weight disulphides such as 2,2'-dipyridyldisulphide, hydroxyethyldisulphide, methyl-2-pyridyldisulphide and sodium tetrathionate and mercurial reagents such as mercuric chloride, p-chloromercuribenzoate and mersalyl. It will be appreciated by those skilled in the art that the affinity between chymopapain and the immobilised inhibitory peptide will differ according to which particular peptide is used, the pH, ionic strength and composition of the elution buffer and the temperature employed. Accordingly, the precise nature and concentration of proteinase inhibitor required to elute chymopapain will also vary. Furthermore, mercurial reagents generally equilibrate with the bound chymopapain more quickly than disulphide reagents and continuous elution may be employed with such inhibitors. Inhibitors which equilibrate only slowly with the bound chymopapain may require incubation of the matrix with the inhibitor, for example for a period 1–2 hours or more, before elution of the chymopapain. However, the protein content and proteinase activity of the eluted fractions may be routinely monitored and the ionic strength or nature of the eluent and incubation time of the matrix with the inhibitor may be varied in order to effectively and selectively displace chymopapain from the matrix. Eluted fractions containing low amounts of protein or low amounts of chymopapain activity may then be discarded.

Preferably the pH of the eluent is sufficiently low to weaken the interaction between chymopapain and the inhibitory peptide, for example pH 4 to 5, more particularly pH 4.5. Suitable eluents have been found to include, for example, hydroxyethyldisulphide (100 mM) in aqueous ethanediol (33%) containing sodium citrate (50 mM) and EDTA (1 mM), pH 4.5; dipyridyldisulphide (30 mM) in aqueous ethanediol (33%) containing sodium citrate (50 mM) and EDTA (1 mM), pH 4.5; methylpyridyldisulphide (30 mM) in aqueous ethanediol (33%) containing sodium citrate (50 mM) and EDTA (1 mM), pH 4.5; mersalyl acid (10 mM) in aqueous ethanediol (33%) containing sodium hydroxide (50 mM) and EDTA (25 mM), adjusted to pH 4.5 with acetic acid; and mercuric chloride (10 mM) in aqueous ethanediol (33%) containing sodium acetate (50 mM), pH 4.5. Mercuric chloride is a particularly preferred reversible cysteine proteinase inhibitor.

The affinity chromatography step in the preferred process according to the invention appreciably increases the specific activity of the chymopapain purified thereby, as measured in terms of activity against BAPNA or by active site titration with E-64 or iodoacetic acid. The active form of chymopapain is preferentially bound and eluted and is thus distinguished from inactive forms of chymopapain and from some other cysteine proteinases present in the crude preparation. Freshly prepared chymopapain according to the invention purified by affinity chromatography generally contains at least 70%, preferably at least 80%, more particularly at least 90% active enzyme.

Generally, purified chymopapain is recovered from the eluate prior to storage or use. Preferably the eluted chymopapain is further purified to displace the cysteine proteinase inhibitor from the active site of the enzyme. The inhibitor may be displaced by the addition of an excess of reducing agent such as cysteine and optionally, if desired, removing the displaced inhibitor using conventional techniques such as gel filtration or dialysis. Alternatively, the inhibitor may be removed by adsorbtion onto a specific resin, for example low molecular weight disulphides may be adsorbed onto a glutathione affinity column and mercurial reagents may be adsorbed onto a chelating resin. Preferably, the inhibitor is removed by activating the enzyme with a reducing agent such as cysteine while it is bound to a cation-exchange column and subsequently washing the inhibitor off the column. Recovered purified chymopapain is preferably lyophilised prior to storage, for example, by freeze-drying.

Chymopapain according to the present invention can be further characterised by methods known to those skilled in the art. Such methods include for example N-terminal amino acid analysis, active site titration with E-64 or iodoacetic acid and rates of inactivation therewith, sodium dodecyl sulphate or multizonal cathodal polyacrylamide gel electrophoresis, and activity against different proteinase substrates.

The novel inhibitory peptides according to the invention may be prepared in a manner analogous to methods known in the art. For example the dipeptide derivatives may be synthesised in a series of stages as follows:

a) The C-terminal of the amino acid intended to form the C-terminal of the inhibitory peptide (the first amino acid) may be protected, for example, by reaction with O,N-dimethylhydroxylamine hydrochloride in the presence of isobutylchloroformate and N-methylmorpholine to give a dimethylhydroxyamide derivative. Preferably the N-terminal of the first amino acid is initially protected with, for example, tertiary butoxycarbonyl.

b) The protected first amino acid, for example a dimethylhydroxyamide derivative, may then be reacted with a strong acid, for example trifluoroacetic acid, to form a quaternary ammonium salt.

c). The quaternary ammonium salt of the protected first amino acid may then be reacted with a second amino acid derivative, for example a N-carbobenzoxy derivative, to form a dipeptide derivative.

d) The dipeptide derivative formed above may be reduced with a mild reducing agent, for example, diisobutylaluminium hydride or lithium aluminium hydride to produce a free aldehyde group at the C-terminal end of the dipeptide.

e) The aldehyde formed above may be derivatised, for example to a semicarbazone by reaction with semicarbazide, to a methoxyimine by reaction with methoxyamine hydrochloride or to an oxime by reaction with hydroxylamine.

f) Finally, the protected N-terminal may be deprotected, for example an N-carbobenzoxy group may be removed by catalytic reduction using 10% palladium on charcoal.

DESCRIPTION OF ANALYTICAL METHODS

PROTEIN DETERMINATION

Where possible, protein concentration was determined by $A_{280}$ using $A_{280, 1}$ =20.0 for papaya latex preparations and $A_{280, 1}$ =18.3 for purified or partially purified chymopapain preparations (Robinson, 1975, Biochemistry 14, 3695–3700). Certain thiol-containing reagents and disulphides tend to absorb at 280 nm. When these were present, the Bio-Rad dye-binding assay (Bio-Rad Laboratories, U.K.) was used to determine protein concentration. Filtered spray-dried papaya latex solutions ($A_{280, 1}$ =20.0) were used as standards. This method is less prone to interference than is $A_{280}$. In purified enzyme preparations protein was estimated by total dry weight of the product.

DETERMINATION OF CHYMOPAPAIN ACTIVITY a) Activity against BAPNA (Assay Method No. 1)—Smith assay Each sample was added to "Buffer 1", aqueous sodium phosphate buffer (0.1M), pH 6.0 containing EDTA (1 mM) and cysteine hydrochloride monohydrate (10 mM), to a final volume of 1.0 ml. The enzyme (where present in the sample) was allowed to activate for 5 minutes at 37° C. before the reaction was started by the addition of 4 ml of N-α-benzoyl-DL-arginine p-nitroanilide (BAPNA) (1.25 mM) substrate solution which had been preheated to 37° C.

N.B. Substrate solution was prepared by dissolving 300 mg BAPNA in warm dimethyl sulphoxide, adding the solution slowly to 450 ml Buffer 1 preheated to 37° C. and then making up to 500 ml with further Buffer 1. Substrate solution was maintained above 30° C. to prevent BAPA precipitation.

Incubation at 37° C. was continued for 30 minutes and then the reaction stopped by the addition of 1 ml acetic acid (4N). Released 4-nitroaniline was determined by measurement of $\Delta A_{410}$. One unit of activity corresponded to the release of 1 picomole of 4-nitroaniline ($\epsilon=8800M^{-1}.cm^{-1}$) per second under these conditions.

These assay conditions correspond to those referred to in GB 2098997 filed in the name of Smith Laboratories Inc. and are used to assay pharmaceutical preparations of chymopapain marketed throughout the world, for example chymopapain sold under the trade name Chymodiactin by The Boots Company PLC, UK and chymopapain sold under the trade name Disken by Sinpoong in South Korea. These activity units are internationally recognised and are commonly referred to as "Smith BAPNA Assay Units".

b) Activity against BAPNA (Assay Method No.2)

Each sample was added to aqueous sodium phosphate buffer (0.10M), pH 6.8, containing EDTA (1 mM) and either dithiothreitol (2 mM) or cysteine (4 mM) to a final volume of 0.975 ml. The enzyme (where present in the sample) was allowed to activate for 5 minutes at 40° C. before the reaction was started by the addition of 25 μl of N-α-benzoyl-DL-arginine p-nitroanilide (BAPNA) (100 mM) in dimethyl sulphoxide. Incubation at 40° C. was continued for 10 minutes and then the reaction stopped by the addition of 1 ml aqueous sodium chloroacetate (0.10M)/sodium acetate (0.20M) buffer, pH 4.3. Released 4-nitroaniline was determined by measurement of $\Delta A_{4.10}$. One unit of activity corresponded to the release of 1 picomole of 4-nitroaniline ($\epsilon=8800M^{-1}.cm^{-1}$) per second under these conditions.

These assay conditions correspond exactly to those described by Buttle & Barrett (1984), loc.cit. and were used in preliminary experiments described in Examples 21, 23 and 26.

The absolute values obtained for chymopapain activity using BAPNA Assay Methods Nos. 1 and 2 differ, the values obtained using Method No. 2 being approximately two to three times higher than the values obtained using Method No.1 (See Example 31).

c) Active-site titration with iodoacetic acid

Active-site titration of chymopapain with iodoacetic acid was carried out in a manner analogous to the active site titration with E-64 described by Zucker et al in Biochim. Biophys. Acta 828 (1985), 196–204. The chymopapain solution was diluted in Buffer 1 as described in (a) above to give a solution containing 60 μM protein ($\epsilon_{280}=4.3284\times10^{4}M^{-1}cm^{-1}$ calculated from $A_{280, 1}$ =18.3, Robinson (1975), loc. cit and MW=23656 calculated from the amino acid sequence of Jacquet et al. (May 1989), Biol. Chem. Hoppe-Seyler, 370, 425–434). 20 μl aliquots of chymopapain solution were placed into titration tubes and incubated for 5 minutes at 37° C. with 20 μl of Buffer 1 (40 μl in control). 20 μl of aqueous iodoacetic acid (10, 20, 30, 40, 50 and 60 μM respectively) was added to each titration tube and the mixture preincubated for 10–20 minutes at 37° C. The reaction was started by the addition of 4 ml of BAPNA substrate solution as described in (a) above which had been preheated to 37° C. Incubation was continued at 37° C. and the reaction stopped after 30 minutes as described in (a) above and released 4-nitroaniline determined by $\Delta A_{410}$. The molar concentration of active chymopapain thus obtained was compared with the molar concentration of protein on the basis of a molar extinction coefficient of $4.3284\times10^{4}M^{-1}cm^{1}$ for chymopapain. The amount of active protein was then expressed as a percentage of the total protein.

d) Activity against azocasein

Activity against azocasein was determined by the method previously described by Rowan et al., (1988), Arch. Biochem. Biophys. 267, 262–270 using less than 1 μM enzyme (based on a mol. wt. of 24,000) and, where desired, 1 μM chicken cystatin. All concentrations of enzymes and inhibitor refer to the concentration of active molecules.

IMMUNOLOGICAL ASSAY BY SINGLE RADIAL IMMUNODIFFUSION

Single radial immunodiffusion assays were based on the method of Mancini et al., 1965, Immunochem 2, 235–254 as follows. Agarose (1% w/v) in aqueous sodium phosphate (10 mM) containing NaCl (0.14M), pH 7.3 containing a mono-specific IgG preparation, was poured on to Gel Bond[R] (FMC Corporation, Maine, USA) and a rectangular pattern of wells (r=1 mm) 1.5 cm apart was cut. The reference and unknown samples were randomly distributed amongst the wells to minimise errors due to edge effects. Following application of antigen to the wells, the plates were left for 24 hours for the precipitin rings to develop. They were then washed, dried and stained. Pure, mildly carboxymethylated antigen was used to generate standard curves, which were plotted as antigen versus the square of ring diameter. The useful range of the assay was 25–300 ng of antigen per well.

PREPARATION OF PPIV AND ANTIBODIES THERETO a) Preparation of affinity column

Butyloxycarbonyl-L-Phe-p-nitrophenyl ester (10 mmol) was added to a stirred mixture of α-$NH_2CH_2CN.HCl$ (20 mmol) and diisopropylethylamine (20 mmol) in dimethylformamide (20 ml). The mixture was stirred at 20° C. for 2 hours and then diluted with ethylacetate (100 ml), washed with water (2×), aqueous triethylamine (5×), water (3×), aqueous potassium bisulphate (2×), water (3×), dried and evaporated. The residue was crystallised from ethylacetate-:hexane to give Boc-L-Phe-$NHCH_2CN$, m.p. 134.5°–135° C.

Ice-cold aqueous trifluoroacetic acid (10 ml) was added to a solution of Boc-L-Phe-$NHCH_2CN$ (5 mmol) in dichloromethane (10 ml). The reaction mixture was incubated at 20° C. for 30 minutes and then the solvent was removed by evaporation at 40° C. The residue was dissolved in chloroform, evaporated and the procedure repeated twice more. The resultant crude trifluoroacetate salt was dissolved in a solution of diisopropylethylamine (7.5 mmol) in dimethyl formamide (10 ml) and Boc-Gly-p-nitrophenyl ester (6.25 mmol) and N-hydroxybenzotriazole monohydrate (6.25 mmol) were added. Sufficient diisopropylethylamine was then added dropwise to generate p-nitrophenol (golden colour) and the mixture was stirred at room temperature for 2 hours. N,N-diethylethylenediamine (1.5 ml) followed after 15 minutes by ethylacetate (60 ml) was added and the mixture was washed with water, aqueous triethylamine, water, aqueous potassium bisulphate, water, dried and evaporated. The residue was purified by chromatography on silica eluted with ethyl acetate:hexane (20:1) to yield Boc-Gly-L-Phe-$NHCH_2CN$ in the form of a foam.

Boc-Gly-L-Phe-$NHCH_2CN$ (30 mg) was dissolved in trifluoroacetic acid:dichloromethane:anisole (25:65:10, 1 ml) and incubated at 0° C. for 30 minutes. The mixture was dried by rotary evaporation at 34° C. and the residue was dissolved in methanol (1.5 ml) and aqueous $NaHCO_3$ (0.1M, pH 8.0, 1.5 ml) to give the ligand solution.

Activated CH-Sepharose$^R$4B Pharmacia; 3 g dry weight) was hydrated overnight in aqueous hydrochloric acid (1 mM, 75 ml) at 4° C. and then washed with hydrochloric acid (1 mM, 600 ml) followed by aqueous $NaHCO_3$ (0.1M, pH 8.0, 300 ml). The gel was suspended in aqueous $NaHCO_3$ (0.1M, pH 8.0, 30 ml), the ligand solution (above) added and the mixture gently agitated overnight at 20° C. The gel was collected on a sintered glass filter, washed with aqueous methanol (50% v/v, 180 ml) and then water (180 ml) and suspended in aqueous ethanolamine (0.1M, 30 ml) adjusted to pH 9.0 with hydrochloric acid. The suspension was shaken for 4 hours at 20° C. and then the gel collected, washed with water (500 ml) and stored in "application" buffer (sodium phosphate (50 mM); EDTA (1 mM); ethanediol (33%), pH 6.8) at 4° C.

b) Purification of PPIV

A column (bed volume 4 ml) of Sepharose$^R$-Ahx-Gly-L-Phe-$NHCH_2CN$ was washed with "elution" buffer (sodium citrate (50 mM); ethanediol (33%), pH 4.5; 12 ml) and then application buffer (see above, 12 ml).

Spray-dried papaya latex (0.5 g) was dissolved in application buffer (10 ml) and filtered (0.22 µm pore). The protein concentration of the filtrate was determined using the Bio-Rad dye-binding assay (Bio-Rad Laboratories, UK). Dithiothreitol was added to the mixture to a final concentration of 2 mM and the mixture incubated at 0° C. for 20 minutes. 80 mg of the latex protein was applied to the column (38 ml/hour/$cm^2$) at 20° C., followed by application buffer (8 ml) and then elution buffer (8 ml). Elution buffer (4 ml) containing hydroxyethyldisulphide (50 mM) was then applied, the flow stopped and the column was left overnight at 20° C. Elution with hydroxyethyldisulphide containing elution buffer was then resumed (10 ml) and eluted fractions (1 ml) were collected. Fractions showing activity against BAPNA were pooled and applied directly on to a Mono S HR 5/5$^R$ (cation-exchange) column which had been pre-equilibrated with aqueous sodium acetate/acetic acid (50 mM), pH 5.0 containing EDTA (1 mM) and then the column was washed with the same buffer (1 ml/min) until the $A_{280\;nm}$ returned to zero. A gradient (12.5 mM $Na^+$/ml) to 1M sodium acetate was then applied to the column (Buttle and Barrett, 1984, loc. cit.) and fractions (1 ml) were collected. Two major protein peaks were eluted, the first peak eluting at about 0.17M $Na^+$ corresponding to papain, and the second peak eluting at about 0.38M $Na^+$ corresponding to PPIV. The PPIV peak fractions were pooled, dialysed against aqueous EDTA (1 mM), freeze-dried and stored at −20° C. Pure PPIV had no detectable activity against BAPNA but was associated with azocasein-digesting activity which was not inhibited by chicken cystatin at a concentration of 1 µM.

c) Preparation of PPIV-specific antibodies

Pure PPIV antigen was mildly carboxymethylated before use by the method described by Zucker et al., 1985, Biochim. Biophys. Acta, 828, 196–204. The antiserum to PPIV was then raised in a rabbit by intramuscular injection of 360 µg of the carboxymethylated protein in Freund's complete adjuvant followed after a fortnight by a subcutaneous injection of 100 µg in incomplete adjuvant. IgG was partially purified from the antisera by ammonium sulphate fractionation as described by Heide and Schwick (1978) in Handbook of Experimental Immunology (Weir, D. M., ed.) Vol. 1, 7.1–7.11, Blackwell, Oxford, followed by dialysis into aqueous sodium phosphate (10 mM) containing NaCl (0.14M), pH 7.3.

The PPIV-specific IgG preparation was used to assay PPIV by single radial immunodiffusion as described hereinbefore.

The following Examples illustrate aspects of the invention more fully by way of example only and should not be considered to limit the scope of the invention in any way.

Abbreviations used herein include ABTS, 2,2'-azinobis(3-ethylbenzthiazoline sulphonic acid); Ahx, 6-aminohexanoyl; Ala, alanine; BAPNA, N-α-benzoyl-DL-arginine p-nitroanilide; Boc, butyloxycarbonyl; CBZ, carbobenzoxy; Cha, cyclohexylalanine; DMF, N,N-dimethylformamide; E-64, L-3-carboxy-2,3-trans-epoxy-proprionylleucylamido-(4-guanidino)butane; EDC, N-ethyl-N'-(3-dimethylaminopropyl)carbodiimide hydrochloride; EDTA, ethylenediaminetetraacetic acid (disodium salt); Gly, glycine; Leu, leucine; Mo, methoxyimine; OBZ, oxybenzyl; Ox, oxime; Phe, phenylalanine; Sc, semicarbazone; THF, tetrahyrofuran; and Tyr, tyrosine.

Bio-Rad, Chelex, Chymodiactin, CH-Sepharose 4B, Chymofast, Disken, ECH-Sepharose, Enzfitter, FPLC, Gel Bond, Mono S HR, S-Sepharose HP, Tween, Zeta and Zetaffinity are all trade names.

All steps were carried out at room temperature unless otherwise indicated.

Example 1

L-alanyl-L-phenylalanyl semicarbazone
Stage a

A) O,N-dimethylhydroxylamine HCl (10.23 g) was added with stirring to dry N,N-dimethylformamide (DMF) (100 ml) at room temperature. N-methylmorpholine (10.6 g) was added over a period of 5 minutes whilst the temperature was maintained below 30° C. A white precipitate formed and the mixture was cooled to 0° C.

B) N-t-Boc-L-Phe (26.5 g) was dissolved in dry tetrahydrofuran (THF) (200 ml) and cooled to −10° C. Isobutylchloroformate (14.38 g) was added to the solution over a period of 5 minutes whilst maintaining the temperature at −10° C. N-methylmorpholine (10.6 g) was added over a period of 10 minutes whilst maintaining the temperature at −10° C. and stirring was continued for a further 10 minutes.

C) Suspension A was added to suspension B over a period of 15 minutes at −10° C. The mixture was allowed to warm to room temperature and then stirred for 3 hours. The resultant mixture was then cooled to 0° C. and 3-dimethylaminopropylamine (10.2 g) added over a period of 5 minutes. Water (200 ml) and ethyl acetate (200 ml) were added and the organic upper layer was separated and sequentially washed with (a) water (200 ml), (b) aqueous $KHCO_3$ (5%, 200 ml), (c) aqueous HCl (0.5N, 200 ml), and (d) water (3×200 ml). The solvent was removed by rotary evaporation under vacuum with the temperature maintained below 30° C. to give N-t-Boc-L-Phe-O,N-dimethylhydroxamate.

Stage b

N-t-Boc-L-Phe-O,N-dimethylhydroxamate (2.9 g) and trifluoroacetic acid (8 ml) were stirred together at room temperature for 4 hours. Excess trifluoroacetic acid was then removed by rotary evaporation under vacuum with the temperature maintained below 30° C. Diethyl ether (30 ml) was added to the residue to form a solution and then the ether was removed under vacuum. The ether treatment was repeated until crystallisation occurred. The solid was collected by filtration, washed with ether and then vacuum dried over $P_2O_5$ to give the trifluoroacetate salt of L-Phe-O,N-dimethylhydroxamate.

Stage c

A) Trifluoroacetate salt of L-Phe-O,N-dimethylhydroxamate (7.15 g) was dissolved in dry DMF (30 ml) with stirring at room temperature. N-methylmorpholine (2.35 g) was added over a period of 5 minutes whilst the temperature was maintained below 30° C. and the resulting mixture was cooled to 0° C.

B) CBZ-L-Ala (4.96 g) was dissolved in dry THF (55 ml) with stirring and the mixture cooled to −10° C. Isobutylchloroformate (3.05 g) was added over a period of 5 minutes at −10° C., N-methylmorpholine (2.35 g) added over a period of 10 minutes and the reaction mixture stirred at −10° C. for a further 10 minutes.

C) Solution A was added to solution B over a 15 minute period at −10° C. and then the temperature of the mixture was allowed to rise to room temperature and stirring continued for 3 hours. The mixture was cooled to 0° C., 3-dimethylaminopropylamine (2.27 g) added over a period of 5 minutes and stirring continued for a further 5 minutes. Water (50 ml) and ethyl acetate (50 ml) were then added, the upper organic phase separated and washed sequentially with (a) water (50 ml ) and saturated aqueous NaCl (5 ml), (b) aqueous $KHCO_3$ (5%, 50 ml), (c) aqueous HCl (0.5N, 50 ml) and (d) water (3×50 ml). The solvent was removed by rotary evaporation under vacuum with the temperature maintained below 30° C. Fresh ethyl acetate (50 ml) was added and then removed by evaporation to give CBZ-L-Ala-L-Phe-O,N-dimethylhydroxamate.

Stage d

CBZ-L-Ala-L-Phe-O,N-dimethylhydroxamate (27.8 g) was dissolved in dry THF (280 ml) and cooled to −70° C. under $N_2$. Diisobutylaluminium hydride in THF (1M, 372 ml) was added under $N_2$ over a period of 60 minutes at −70° C. and stirring was continued for a further 60 minutes at −70° C. The reaction was quenched into saturated aqueous NaCl (400 ml) and Rochell-salt solution (600 ml) with stirring at 0° C. under $N_2$ and the mixture then allowed to warm to room temperature. Ethyl acetate (600 ml) was added, the mixture filtered and the aqueous layer separated and extracted with ethyl acetate (200 ml). The combined organic phases were washed with water (600 ml)/saturated aqueous NaCl (400 ml) (×3). The solvent was removed by rotary evaporation under vacuum with the temperature maintained below 30° C. The residue was recrystallised from toluene and the solid was vacuum dried over $P_2O_5$ to give CBZ-L-Ala-L-Phe aldehyde.

Stage e

A) CBZ-L-Ala-L-Phe aldehyde (3 g) was dissolved in industrial methylated spirit (20 ml). The solution was heated to 50° C. and filtered to remove insolubles.

B) A solution of semicarbazide HCl (1.3 g) in water (10 ml) was added to a solution of $KHCO_3$ (1.1g) in water (10 ml).

C) Solution B was added to solution A and the resultant mixture stirred at 50° C. for 2 hours. Ethyl acetate (50 ml) and water (100 ml) were added, the aqueous layer separated and extracted with ethyl acetate (2×20 ml) and the combined organic phases washed sequentially with (a) aqueous $KHCO_3$ (5%, 50 ml); (b) aqueous HCl (0.5N, 50 ml) and (c) water/saturated aqueous NaCl (50 ml/20 ml×3). The solvent was removed by rotary evaporation under vacuum with the temperature maintained below 30° C. to give CBZ-L-Ala-L-PheSc.

stage f

CBZ-L-Ala-L-PheSc (680 mg) was dissolved in methanol (90 ml) and insolubles were removed by filtration. The apparatus containing the methanolic solution of CBZ-L-Ala-L-PheSc was purged with $N_2$ and the catalyst, 10% palladium on charcoal (100 mg) was added. $H_2$ was passed into the closed system for 75 minutes. The catalyst was removed by filtration and the methanol was removed by rotary evaporation under vacuum with the temperature maintained below 30° C. The residue crystallised on standing and the solid was vacuum dried over $P_2O_5$ to give L-alanyl-L-phenylalanyl semicarbazone (L-Ala-L-PheSc).

Example 2

L-phenylalanyl-L-phenylalanyl semicarbazone

Stages a and b

The trifluoroacetate salt of L-Phe-O,N-dimethylhydroxamate was prepared in accordance with stages a and b of Example 1.

Stage c

A). Trifluoroacetate salt of L-Phe-O,N-dimethylhydroxamate (1.932 g) was dissolved in dry DMF (8 ml) with stirring at room temperature. N-methyl-morpholine (0.606 g) was added over a period of 5 minutes whilst the temperature was maintained below 30° C. and the resulting mixture was cooled to 0° C.

B) CBZ-L-Phe (1.794 g) was dissolved in dry THF (15 ml) with stirring and the mixture cooled to −10° C.

Isobutylchloroformate (0.822 g) was added over a period of 5 minutes at –0° C., N-methylmorpholine (0.606 added over a period of 10 minutes and the reaction mixture stirred at –10° C. for a further 10 minutes.

C) Solution A was added to solution B over a 15 minute period at –10° C. and then the temperature of the mixture was allowed to rise to room temperature and stirring continued for 3 hours. The mixture was cooled to 0° C., 3-dimethylaminopropylamine (0.612 g) added over a period of 5 minutes and stirring continued for a further 5 minutes. Water (20 ml) and ethyl acetate (30 ml) were then added, the organic phase separated and washed sequentially with (a) aqueous $KHCO_3$ (5%, 20 ml), (b) aqueous HCl (0.5N, 20 ml) and (c) water (2×30 ml). The solvent was removed by rotary evaporation under vacuum with the temperature maintained below 35° C. and the residue was recrystallised from isopropyl alcohol to give CBZ-L-Phe-L-Phe-O,N-dimethylhydroxamate.

Stage d

CBZ-L-Phe-L-Phe-O,N-dimethylhydroxamate (4.89 g) was dissolved in dry THF (40 ml). A dry flask was charged with lithium aluminium hydride (0.493 g) and dry THF (20 ml) added under $N_2$ and stirred at room temperature for 10 minutes before cooling to –50° C. The solution of hydroxamate in dry THF was then added over a period of 10 minutes at –50° C. under $N_2$ and stirring was continued for a further 20 minutes at 0°–5° C.

The reaction mixture was cooled to –50° C. and saturated Rochell salt solution (60 ml) was added under $N_2$. The mixture was allowed to warm to room temperature, HCl (conc., 10 ml) added to bring the aqueous phase to pH 3, and the insolubles removed by filtration. Ethyl acetate (50 ml) was added and the organic phase separated and washed sequentially with (a) water (50 ml), (b) aqueous $KHCO_3$ (5%, 50 ml), (c) aqueous HCl (0.5N, 50 ml) and (d) water (3×50 ml). The ethyl acetate was then removed by rotary evaporation under vacuum with the temperature maintained below 30° C. The residue was left to stand overnight, vacuum dried over $P_2O_5$ and finally crystallised from toluene to give CBZ-L-Phe-L-Phe aldehyde.

Stage e

A) CBZ-L-Phe-L-Phe aldehyde (0.645 g) was dissolved in industrial methylated spirit (10 ml) at 70° C.

B) Sodium acetate trihydrate (0.224 g) was added to a solution of semicarbazide HCl (0.183 g) in water (3 ml), industrial methylated spirit (2 ml) was added and the mixture warmed to 60° C.

C) Solution A was added to solution B and the flask containing A washed with further industrial methylated spirit (3 ml) and the washings added to the mixture which was stirred at 60°–70° C. for 30 minutes. The mixture was allowed to cool slowly for 1 hour, left to stand on ice for a further hour, and finally left overnight at 4° C. The solid was collected by filtration, washed with industrial methylated spirit:water (4:1, 3 ml) and vacuum dried over $P_2O_5$ to give CBZ-L-Phe-L-PheSc.

Stage f

CBZ-L-Phe-L-PheSc (2.1 g) was dissolved in methanol (315 ml) at 30° C. and the insolubles removed by filtration. The apparatus containing the methanolic solution of the semicarbazone was purged with $N_2$, the catalyst 10% palladium on charcoal (0.35 g) was added and $H_2$ was passed into the closed system for 30 minutes. The catalyst was removed by filtration and the solvent removed by rotary evaporation under vacuum with the temperature maintained below 30° C. The residue was vacuum dried over $P_2O_5$ to give L-phenylalanyl-L-phenylalanyl semicarbazone (L-Phe-L-PheSc).

Example 3

L-Phenylalanyl-L-phenylalanyl methoxyimine

Stages a–d

CBZ-L-Phe-L-Phe aldehyde was prepared as described Example 2, stages a–d.

Stage e

A) CBZ-L-Phe-L-Phe aldehyde (0.645 g) was dissolved in industrial methylated spirit (35 ml) at 60°–65° C. and filtered to remove insolubles.

B) Sodium acetate trihydrate (0.224 g) was added to a solution of methoxylamine HCl (0.138 g) in water (25 ml) at 60° C.

C) Solution B was added to solution A, the flask containing B washed with water (10 ml) at 60° C., the washings combined with the mixture and heated at 60° for ½ hour, then left to cool at room temperature for 2 hours. The solid was collected by filtration, washed with industrial methylated spirit:water (1:1, 6 ml) and vacuum dried over $P_2O_5$ to give CBZ-L-Phe-L-Phe-methoxyimine.

Stage f

CBZ-L-Phe-L-Phe-methoxyimine (550 mg) was dissolved in methanol (300 ml) and the insolubles removed by filtration. The apparatus containing the methanolic methoxyimine was purged with $N_2$, and the catalyst 10% palladium on charcoal (100 mg) was then added. $H_2$ was passed into the sealed vessel and recharged as necessary for 4½ hours. The catalyst was removed by filtration and the solvent removed by rotary evaporation under vacuum with the temperature maintained below 30° C. to give L-phenylalanyl-L-penylalanyl-methoxyimine (L-Phe-L-PheMo).

Example 4

L-Phenylalanyl-D-phenylalanyl semicarbazone

Stage a

A) O,N-dimethylhydroxylamine HCl (3.891 g) was suspended in dry DMF (40 ml) at room temperature. N-methylmorpholine (4.032 g) was added over a period of 5 minutes whilst the temperature was maintained below 30° C. and the mixture was then cooled with stirring to 0° C.

B) N-t-Boc-D-Phe (10.08 g) was dissolved in dry THF (80 ml) and cooled to –10° C. Isobutylchloroformate (5.47 g) was added to the solution over a period of 5 minutes whilst maintaining the temperature at –10° C. N-methylmorpholine (4.032 g) was added over a period of 10 minutes whilst maintaining the temperature at –10° C. and stirring was continued for a further 10 minutes.

C) Suspension A was added to suspension B over a period of 15 minutes at –10° C., the mixture allowed to warm to room temperature and stirred for 3 hours. The mixture was then cooled to 0° C., 3-dimethylaminopropylamine (3.88 g) added over a period of 5 minutes, and stirring continued for a further 5 minutes. Water (60 ml) and ethyl acetate (60 ml) were added, the organic layer separated and washed sequentially with (a) water (60 ml), (b) aqueous $KHCO_3$ (5%, 60 ml), (c) aqueous HCl (0.5M, 60 ml) and (d) water (3×60 ml). The solvent was removed by rotary evaporation under vacuum whilst the temperature was maintained below 30° C. to give N-t-Boc-D-Phe-O,N-dimethylhydroxamate.

Stage b

N-t-Boc-D-Phe-O,N-dimethylhydroxamate (11.3 g) was cooled on ice, trifluoroacetic acid (30 ml) added and the mixture stirred at room temperature for 3 hours. Excess trifluoroacetic acid was removed by rotary evaporation under vacuum with the temperature maintained below 30° C. and diethyl ether (100 ml) added to the residue to form a solution. The solvent was removed under vacuum and the process repeated until crystallisation occurred. The solid was collected by filtration, washed with diethyl ether and vacuum dried over $P_2O_5$ to give the trifluoroacetate salt of D-Phe-O,N-dimethylhydroxamate.

Stage c

A) Trifluoroacetate salt of D-Phe-O,N-dimethylhydroxamate (10.1 g) was dissolved in dry DMF (41 ml) with stirring at room temperature. N-methylmorpholine (3.755 g) was added over a period of 5 minutes whilst the temperature was maintained below 30° C. and the resulting mixture was cooled to 0° C.

B) CBZ-L-Phe (9.4 g) was dissolved in dry THF (80 ml) with stirring and the mixture cooled to −10° C. Isobutylchloroformate (4.307 g) was added over a period of 5 minutes at −10° C., N-methylmorpholine (3.155 g) added over a period of 10 minutes and the reaction mixture stirred at −10° C. for a further 10 minutes.

C) Solution A was added to solution B over a 15 minute period at −10° C. and then the temperature of the mixture allowed to rise to room temperature and stirring continued for 3 hours. The mixture was cooled to 0° C., 3-dimethyl-aminopropylamine (3.20 g) added over a period of 5 minutes and stirring continued for a further 5 minutes. Water (60 ml) and ethyl acetate (60 ml) were then added, the organic phase separated and washed sequentially with (a) water (60 ml) and saturated aqueous NaCl (60 ml), (b) aqueous $KHCO_3$ (5%, 60 ml), (c) aqueous HCl (0.5N, 60 ml) and (d) water (3×60 ml). The solvent was removed by rotary evaporation under vacuum with the temperature maintained below 30° C. Fresh ethyl acetate was added and then removed by evaporation. The residue was recrystallised from isopropanol to give CBZ-L-Phe-D-Phe-O,N-dimethylhydroxamate.

Stage d

Diisobutylaluminium hydride in dichloromethane (1M, 10 ml) was added to an $N_2$-purged flask. The flask was warmed to 50° C. until all the dichloromethane had evaporated and the system was again purged with $N_2$. dry THF (10 ml) was added and the mixture cooled to −70° C. CBZ-L-Phe-D-Phe-O,N-dimethylhydroxamate (0.978 g) was dissolved in dry THF (10 ml) and added over a period of 10 minutes at −70° C. to the diisobutylaluminium hydride solution and stirring was continued for a further 10 minutes at −70° C. The reaction mixture was quenched into methanol (30 ml) and saturated Rochell salt solution (30 ml) at −60° C. and the mixture was allowed to warm to room temperature. Water (50 ml) and ethyl acetate (50 ml) were added and the organic phase was separated and the aqueous phase was extracted with ethyl acetate (50 ml). The combined organic phases were washed with water (2×200 ml) and filtered. The organic phase was separated and the solvent removed by rotary evaporation under vacuum with the temperature maintained below 30° C. Fresh ethyl acetate was added and then removed to give CBZ-L-Phe-D-Phe aldehyde.

Stage e

A) CBZ-L-Phe-D-Phe aldehyde (400 mg) was dissolved in industrial methylated spirit (10 ml) at 60° C.

B) Sodium acetate trihydrate (0.298 g) in water (3 ml) at 60° C. was added to a solution of semicarbazide HCl (0.244 g) in water (3 ml) at 60° C.

C) Solutions A and B were combined and the resultant mixture stirred at 60° C. for 5 hours before leaving to stand overnight at 4° C. The solid was collected by filtration and dried in vacuo over $P_2O_5$ to give CBZ-L-Phe-D-PheSc.

Stage f

CBZ-L-Phe-D-PheSc (600 mg) was dissolved in methanol (90 ml) and the insolubles removed by filtration. The apparatus containing the methanolic semicarbazone solution was purged with $N_2$, and the catalyst 10% palladium on charcoal (100 mg) was added. $H_2$ was charged into the closed vessel for 2 hours. The catalyst was removed by filtration and the methanol removed by rotary evaporation under vacuum whilst the temperature was maintained below 30° C. to give L-phenylalanyl-D-phenylalanyl semicarbazone (L-Phe-D-PheSc).

Example 5

L-phenylalanyl-L-phenylalanyl oxime

Stages a–d

CBZ-L-Phe-L-Phe aldehyde was prepared as described in Example 2, stages a–d.

Stage e

A) CBZ-L-Phe-L-Phe aldehyde prepared as described above (0.645 g) was dissolved in industrial methylated spirit (35 ml) at 60°–65° C. and the solution filtered to remove insolubles.

B) Sodium acetate trihydrate (0.224 g) was added to a solution of hydroxylamine HCl (0.114 g) in water (25 ml) at 60° C.

C) Solution B was added to solution A and the flask containing B washed with water (10 ml) and the washings added to the mixture which was then stirred at 60°–65° C. for ¾ hour and then cooled for 2–3 hours at 4° C. The solid was filtered off, washed with industrial methylated spirit/water (1:1, 5 ml) and vacuum dried over $P_2O_5$ to give CBZ-L-Phe-L-PheOx as a mixture of syn- and anti- isomers.

Stage f

CBZ-L-Phe-L-PheOx (500 mg) was dissolved in methanol (130 ml) and insolubles removed by filtration. The apparatus containing the methanolic oxime was purged with $N_2$ and the catalyst, 10% palladium on charcoal (83 mg) was added. $H_2$ was then charged into the sealed vessel for 30 minutes. The catalyst was removed by filtration and the solvent removed by rotary evaporation under vacuum with the temperature maintained below 30° C. Further solvent was removed using a high vacuum pump and the residue vacuum dried over $P_2O_5$ to give L-phenylalanyl-L-phenylalanyl oxime (L-Phe-L-PheOx).

Example 6

L-alanyl-D-phenylalanyl semicarbazone

Stages a and b

The trifluoroacetate salt of D-Phe-O,N-dimethylhydroxamate was prepared in accordance with stages a and b of Example 4.

Stage c

A) The trifluoroacetate salt of D-Phe-O,N-dimethylhydroxamate (5.000 g) was dissolved in dry THF (20 ml). N-methylmorpholine (1.578 g) was added slowly whilst maintaining the temperature below 30° C. and the resulting mixture was cooled to 0° C.

B) CBZ-L-Ala (3.463 g) was dissolved in dry THF (40 ml) with stirring and the mixture cooled to −10° C. Isobutylchloroformate (2.158 g) was added over a period of 5 minutes at −10° C., N-methylmorpholine (1.578 g) added over a period of 10 minutes and the reaction mixture stirred at −10° C. for a further 10 minutes.

C) The two solutions, A and B, were mixed at −10° C. over a 10 minute period and then the temperature of the mixture was allowed to rise to room temperature and stirring continued for 3 hours. The mixture was cooled to 0° C., 3-dimethylaminopropylamine (1.585 g) added and the reaction was quenched with water (50 ml). Ethyl acetate (50 ml) was added, the organic phase was separated and the aqueous layer extracted with ethyl acetate (2×30 ml). The organic layers were combined and washed sequentially with (a) water (50 ml) and saturated aqueous NaCl (10 ml), (b) aqueous $KHCO_3$ (5%, 50 ml), (c) aqueous HCl (0.5N, 50 ml) and (d) water (3×50 ml). The solvent was removed by rotary evaporation under vacuum with the temperature maintained below 30° C. The solid was recrystallised from ethyl acetate to give CBZ-L-Ala-D-Phe-O,N-dimethylhydroxamate.

Stage d

CBZ-L-Ala-D-Phe-O,N-dimethylhydroxamate (2.9 g) was dissolved in dry THF (25 ml). The solution was cooled to −70° C. under nitrogen. Diisobutylaluminium hydride in THF (1M, 37 ml) was added over a period of 10 minutes at −70° C. and stirring was continued for a further 10 minutes.

The reaction was quenched into saturated Rochell salt solution (125 ml) and THF (125 ml) with stirring at −30° C. under an $N_2$ purge and the mixture then allowed to warm to room temperature. Ethyl acetate (100 ml) was added and the organic phase was separated. The aqueous layer was extracted with ethyl acetate (2×30 ml) and the organic layers combined and washed with water (3×100 ml). The reaction mixture was filtered and the solvent removed by rotary evaporation under vacuum with the temperature maintained below 30° C. Fresh ethyl acetate was added and then removed to give CBZ-L-Ala-D-Phe aldehyde.

Stage e

A) CBZ-L-Ala-D-Phe aldehyde (1.2 g) was dissolved in THF (20 ml) and industrial methylated spirit (20 ml) and heated to 50° C.

B) A hot solution of semicarbazide HCl (1.8 g) in water (15 ml) was added to a hot solution of $KHCO_3$ (1.5 g) in water (15 ml).

C) Solution B was added to solution A and the resultant mixture stirred at 50° C. for 4 hours. The solvent was removed by rotary evaporation under vacuum with the temperature maintained below 30° C. Water (50 ml) was added to the residue, the solid collected by filtration, washed with water:industrial methylated spirit (1:1) and vacuum dried over $P_2O_5$ to give CBZ-L-Ala-D-PheSc.

Stage f

CBZ-L-Ala-D-PheSc (750 mg) was dissolved in methanol (50 ml) and insolubles were removed by filtration. The apparatus containing the methanol solution was purged with $N_2$ and the catalyst, 10% palladium on charcoal (100 mg) was added. $H_2$ was passed into the closed system for 90 minutes. The catalyst was removed by filtration and the solvent was removed by rotary evaporation under vacuum with the temperature maintained below 30° C. and vacuum dried over $P_2O_5$ to give L-alanyl-D-phenylalanyl semicarbazone (L-Ala-D-PheSc).

Example 7

L-tyrosinyl-L-phenylalanyl semicarbazone

Stages a and b

The trifluoroacetate salt of L-Phe-O,N-dimethyl hydroxamate was prepared in accordance with stages a and b of Example 4.

Stage c

A) The trifluoroacetate salt of L-Phe-O,N-dimethyl hydroxamate (7.95 g) was dissolved in dry DMF (30 ml) with stirring at room temperature. N-methylmorpholine (2.49 g) was added over a period of 5 minutes whilst the temperature was maintained below 30° C. and the resulting mixture was cooled to 0° C.

B) CBZ-OBZ-L-Tyr (10 g) was dissolved in dry DMF (60 ml) with stirring and the mixture cooled to −10° C. Isobutylchloroformate (3.39 g) was added over a period of 5 minutes at −10° C. N-dimethylmorpholine (2.49 g) was added over a period of 10 minutes and the reaction mixture stirred at −10° C. for a further 10 minutes.

C) Solution A was added to solution B over a 15 minute period at −10° C. and then the temperature of the mixture allowed to rise to room temperature and stirring continued for 3 hours. The mixture was cooled to 0° C. and 3-dimethylaminopropylamine (2.52 g) added over a period of 5 minutes. Water (50 ml) and ethyl acetate (50 ml) were then added, the upper organic phase separated and washed sequentially with (a) water (50 ml), (b) aqueous $KHCO_3$ (5%, 50 ml), (c) aqueous HCl (0.5M, 50 ml) and (d) water (3×50 ml). The solvent was removed by rotary evaporation under vacuum with the temperature maintained below 30° C. and the residue was recrystallised from isopropyl alcohol to give CBZ-OBZ-L-Tyr-L-Phe-O,N-dimethylhydroxamate.

Stage d

CBZ-OBZ-L-Tyr-L-Phe-O,N-dimethylhydroxamate (1.012 g) was dissolved in dry THF (10 ml). Diisobutylaluminium hydride in THF (1M, 8.5 ml) was added under $N_2$ over a period of 10 minutes at −70° C. and stirring was continued for a further 10 minutes.

The reaction was quenched into methanol (20 ml) and Rochell salt solution (30 ml) with stirring at −60° C. under $N_2$ and the mixture then allowed to warm to room temperature. Water (50 ml) and ethyl acetate (50 ml) were added and the organic phase was separated and washed with water (200 ml). The reaction mixture was filtered and the solvent was removed from the filtrate by rotary evaporation under vacuum with the temperature maintained below 30° C. Fresh ethyl acetate was then added and removed by rotary evaporation. The resulting solid was vacuum dried over $P_2O_5$ to give CBZ-OBZ-L-Tyr-L-Phe aldehyde.

Stage e

A) CBZ-OBZ-L-Tyr-L-Phe aldehyde (400 mg) was dissolved in industrial methylated spirit (20 ml) and THF (10 ml) and heated to 60° C.

B) A hot solution of semicarbazide HCl (600 mg) in water (5 ml) was added to a hot solution of $KHCO_3$ (500 mg) in water (5 ml).

C) Solution B was added to solution A and the resultant mixture stirred at 60° C. for 2 hours. The solvent was removed by rotary evaporation under vacuum with the temperature maintained below 30° C. and the residue quenched with water. The solid was collected by filtration, washed with water and industrial methylated spirit and vacuum dried over $P_2O_5$ to give CBZ-OBZ-L-Tyr-L-PheSc.

Stage f

CBZ-OBZ-L-Tyr-L-PheSc (770 mg) was dissolved in dry THF (70 ml), filtered and then methanol (20 ml) added to the filtrate. The apparatus containing the semicarbazone solution was purged with $N_2$ and the catalyst, 10% palladium on charcoal (100 mg) was added. $H_2$ was passed into the closed system for several hours. The catalyst was removed by filtration and the solvent removed by evaporation to give L-tyrosinyl-L-phenylalanyl semicarbazone (L-Tyr-L-PheSc).

Example 8

L-alanyl-L-cyclohexylalanyl semicarbazone

Stage a

A) O,N-dimethylhydroxylamine HCl (8.51 g) was added with stirring to dry DMF (75 ml) and N-methylmorpholine (8.8 g) added over a period of 5 minutes whilst the temperature was maintained below 30° C. A white precipitate formed and the mixture was cooled to 0° C.

B) N-t-Boc-L-Cha (22.5 g) was dissolved in dry THF (200 ml) and cooled to −10° C. Isobutylchloroformate (11.94 g) was added over a period of 5 minutes whilst maintaining the temperature at −10° C. N-methylmorpholine (8.8 g) was added over a period of 10 minutes whilst maintaining the temperature at −10° C. and stirring was continued for a further 10 minutes.

C) Suspension A was added to suspension B over a period of 15 minutes at −10° C. and then the mixture allowed to warm to room temperature and stirred for 4 hours. The mixture was cooled to 0° C. and 3-dimethylaminopropylamine (8.6 g) added over a period of 5 minutes and stirring continued for a further 5 minutes. Water (200 ml) and ethyl acetate (100 ml) were added and the aqueous layer separated and extracted with ethyl acetate (2×100 ml). The combined organic phases were sequentially washed with (a) water (100 ml) and saturated aqueous NaCl (20 ml), (b) aqueous $KHCO_3$ (5%, 100 ml), (c) aqueous HCl (0.5N, 100 ml), and (d) water (3×100 ml). The solvent was removed by rotary evaporation under vacuum with the temperature maintained below 30° C. to give N-t-Boc-L-Cha-O,N-dimethylhydroxamate.

Stage b

N-t-Boc-L-Cha-O,N-dimethylhydroxamate (26 g) and trifluoroacetic acid (65 ml) were stirred at 0° C. for 5 minutes and then the temperature of the mixture allowed to rise to room temperature and stirring continued for 3 hours. The excess trifluoroacetic acid was then removed by rotary evaporation under vacuum with the temperature maintained below 30° C. Diethyl ether was added to the residue to form a solution and then the ether was removed under vacuum. The ether treatment was repeated to give a yellow oil of the trifluoroacetate salt of L-Cha-O,N-dimethylhydroxamate.

Stage c

A) Trifluoroacetate salt of L-Cha-O,N-dimethylhydroxamate (17 g) was dissolved in dry THF (50 ml). N-methyl-morpholine (3.95 g) was added over a period of 5 minutes whilst the temperature was maintained below 30° C. and the mixture then cooled to 0° C.

B) CBZ-L-Ala (9.25 g) was dissolved in dry THF (700 ml) with stirring and the mixture cooled to −10° C. Isobutylchloroformate (5.35 g) was added over a period of 5 minutes at −10° C., N-methylmorpholine (3.95 g) added over a period of 10 minutes and the reaction mixture stirred at −70° C. for a further 10 minutes.

C) Solution A was added to solution B over a 15 minute period at −70° C. and then the temperature of the mixture was allowed to rise to room temperature and stirring continued for 3 hours. The mixture was cooled to 0° C., 3-dimethylaminopropylamine (3.98 g) added over a period of 5 minutes and stirring continued for a further 5 minutes. Water (150 ml) and ethyl acetate (150 ml) were then added and the aqueous phase separated and extracted with ethyl acetate (2×75 ml). The combined organic phases were sequentially washed with (a) water (125 ml), (b) aqueous $KHCO_3$ (5%, 125 ml), (c) aqueous HCl (0.5N, 125 ml) and (d) water (3×725 ml). The solvent was removed by rotary evaporation with the temperature maintained below 30° C. Fresh ethyl acetate was added and removed by evaporation to give CBZ-L-Ala-L-Cha-O,N-dimethylhydroxamate.

Stage d

CBZ-L-Ala-L-Cha-O,N-dimethylhydroxamate (7.22 g) was dissolved in dry THF (160 ml) and cooled to −70° C. under $N_2$. Diisobutylaluminium hydride in THF 86 ml) was added under $N_2$ over a period of 20 minutes at −70° C. and stirring was continued for a further 20 minutes.

The reaction was quenched into Rochell salt solution (400 ml) with stirring at 0° C. under $N_2$ and the mixture then allowed to warm to room temperature. Ethyl acetate (150 ml) was added and the mixture stirred for 5 minutes. The reaction mixture was filtered, the organic layer separated and the aqueous phase extracted with ethyl acetate (2×50 ml). The combined organic phases were washed with water (3×200 ml) with saturated aqueous NaCl added to the final washes. Solvent was removed by rotary evaporation with the temperature maintained below 30° C. to give an oil of CBZ-L-Ala-L-Cha aldehyde.

Stage e

A) CBZ-L-Ala-L-Cha aldehyde (8 g) was dissolved in industrial methylated spirit (50 ml) and heated to 50° C.

B) A hot solution of semicarbazide HCl (3.0 g) in water (25 ml) was added to a hot solution of $KHCO_3$ (2.67 g) in water (25 ml).

C) Solution B was added to solution A and the resultant mixture stirred at 50° C. for 3 hours. The mixture was allowed to cool and stood overnight at 4° C. Most of the industrial methylated spirit was removed by rotary evaporation with the temperature maintained below 30° C. and ethyl acetate (50 ml) added to the residue. The organic phase was separated and washed sequentially with (a) water (30 ml), (b) aqueous $KHCO_3$ (5%, 30 ml), (c) aqueous HCl (0.5N, 30 ml) and (d) water (2×50 ml) with saturated aqueous NaCl added as required to aid separation. The solvent was removed by rotary evaporation with the temperature maintained below 30° C. and the solid recrystallised from isopropanol and ether to give CBZ-L-Ala-L-ChaSc.

Stage f

CBZ-L-Ala-L-ChaSc (900 mg) was dissolved in methanol (30 ml) and the catalyst, 10% palladium on charcoal (100 mg), was added under $N_2$. $H_2$ was passed into the closed system for 6 hours and then the catalyst removed by filtration. Solvent was removed by rotary evaporation with the temperature maintained below 30° C. and the solid washed with ether and vacuum dried over $P_2O_5$ to give L-Alanyl-L-cyclohexylalanine semicarbazone (L-Ala-L-ChaSc).

Example 9

L-alanyl-L-leucinyl semicarbazone

Stage a

A) O,N-dimethylhydroxylamine HCl (9.17 g) was added with stirring to dry DMF (110 ml) at room temperature. N-methylmorpholine (9.5 g) was added over a period of 5 minutes whilst the temperature was maintained below 30° C. A precipitate formed and the mixture was cooled to 0° C.

B) N-t-Boc-L-Leu (23.3 g) was dissolved in dry THF (220 ml) and cooled to −10° C. Isobutylchloroformate (12.90 g) was added over a period of 5 minutes whilst maintaining the temperature at −10° C. N-methylmorpholine (9.51 g) was added over a period of 10 minutes whilst maintaining the temperature at −10° C. and stirring was continued for a further 10 minutes.

C) Suspension A was added to suspension B over a period of 15 minutes at −10° C. The mixture was allowed to warm to room temperature and stirred for 3 hours. The mixture was then cooled to 0° C. and 3-dimethylaminopropylamine (9.13 g) was added over a period of 5 minutes and stirring continued for a further 5 minutes. Ethyl acetate (110 ml) and water (110 ml) were added and the organic layer separated and washed sequentially with (a) water (2×100 ml), (b) aqueous $KHCO_3$ (5%, 100 ml), (c) aqueous HCl (0.5N, 100 ml) and (d) water (3×100 ml). The solvent was removed by rotary evaporation with the temperature maintained below 30° C. to give N-t-Boc-L-Leu-O,N-dimethylhydroxamate Stage b N-t-Boc-L-Leu-O,N-dimethylhydroxamate (23.4 g) and trifluoroacetic acid (165 ml, cooled to 0° C.) were stirred together at room temperature for 18 hours. The excess trifluoroacetic acid was then removed by rotary evaporation with the temperature maintained below 30° C. Diethyl ether was added to the residue to form a solution and then the ether was removed under vacuum. This was repeated until crystallisation at 4° C. occurred to give the trifluoroacetate salt of L-Leu-O,N-dimethylhydroxamate.

Stage c

A) Trifluoroacetate salt of L-Leu-O,N-dimethylhydroxamate (1.8 g) was dissolved in dry THF (10 ml) with stirring at room temperature. The mixture was cooled to 0° C. and N-methylmorpholine (0.635 g) was added over a period of 5 minutes.

B) CBZ-L-Ala (1.40 g) was dissolved in dry THF (20 ml) and cooled to −10° C. Isobutylchloroformate (0.869 g) was added over a period of 5 minutes at −10°, N-methyl-morpholine (0.635 g) added over a period of 10 minutes and the reaction mixture stirred at −10° C. for a further 10 minutes.

C) Solution A was added to solution B over a period of 15 minutes at −10° C. and then the temperature of the mixture was allowed to rise to room temperature and stirring continued for 18 hours. The mixture was cooled to 0° C., 3-dimethylaminopropylamine (0.64 g) added and then the reaction mixture quenched with water (25 ml) and ethyl acetate (25 ml). The aqueous phase was separated and extracted with ethyl acetate (2×25 ml).

The combined organic phases were washed sequentially with (a) water (50 ml) and saturated aqueous NaCl (to aid separation (b) aqueous $KHCO_3$ (5%, 30 ml), (c) aqueous HCl (0.5N, 30 ml) and (d) water (3×30 ml). The solvent was removed by rotary evaporation with the temperature maintained below 30° C. and the solid vacuum dried over $P_2O_5$ to give CBZ-L-Ala-L-Leu-O,N-dimethylhydroxamate.

Stage d

CBZ-L-Ala-L-Leu-O,N-dimethylhydroxamate (1.9 g) was dissolved in dry THF (40 ml) and cooled to −70° C. under $N_2$. Diisobutylaluminium hydride in THF (1M, 29.5 ml) was added under $N_2$ over a period of 10 minutes at −70° C. and stirring was continued for a further 10 minutes.

The reaction was quenched into methanol (50 ml) and Rochell salt solution (50 ml) with stirring at −60° C. under $N_2$ and the mixture then allowed to warm to room temperature. Water (50 ml) and ethyl acetate (50 ml) were added, the mixture filtered and the aqueous layer sparated and extracted with ethyl acetate (2×50 ml). The combined organic phases were washed with water (3×100 ml) and saturated aqueous NaCl to aid separation. The solvent was removed by rotary evaporation with the temperature maintained below 30° C., fresh ethyl acetate added and then removed by rotary evaporation to give CBZ-L-Ala-L-Leu aldehyde.

Stage e

A) CBZ-L-Ala-L-Leu aldehyde (6.7 g) was dissolved in industrial methylated spirit (50 ml) and warmed to 50° C.

B) A hot solution of $KHCO_3$ (9 g) in water (30 ml) was added to a hot solution of semicarbazide HCl (10.8 g) in water (30 ml).

C) Solution B was added to solution A and the mixture stirred at 50° C. for 3 hours and left to stand overnight at room temperature. The solid was filtered off, washed with industrial methylated spirit:water (1:1, 20 ml) and vacuum dried over $P_2O_5$ to give CBZ-L-Ala-L-LeuSc.

Stage f

CBZ-L-Ala-L-LeuSc (950 mg) was dissolved in methanol (100 ml). and insolubles were removed by filtration. Further methanol (50 ml) was added and the apparatus purged with $N_2$. The catalyst, 10% palladium on charcoal (100 mg) was added under $N_2$ and then $H_2$ passed into the closed system for 135 minutes. The catalyst was removed by filtration and solvent removed by rotary evaporation with the temperature maintained below 30° C. The solid was vacuum dried over $P_2O_5$ to give L-alanyl-L-leucinyl semicarbazone (L-Ala-L-LeuSc).

Example 10

Preparation of active site directed affinity chromatography matrix-ECH-Sepharose 4B-L-Ala-L-PheSc ECH-Sepharose$^R$ 4B (3 g wet weight) was washed on a sintered glass filter with aqueous NaCl (0.5M, 240 ml) followed by water (120 ml). N-Ethyl-N'-(3-dimethylaminopropyl)carbodiimide hydrochloride (EDC) was dissolved in water to give a 0.1M EDC solution and the pH of the EDC solution was stabilised to pH 4.5 by the addition of hydrochloric acid or solid sodium acetate. L-Ala-L-PheSc (10 mg), prepared as described in Example 1, was dissolved in methanol (400 μl) and added to the washed gel together with aqueous EDC (0.1M, 2.4 ml ). The mixture was agitated gently at 20° C. for 1 hour, the pH readjusted to pH 4.5 if required and agitation continued at 20° C. for 23 hours. L-Glycine was then added to a final concentration of 1M and agitation at 20° C. continued for a further 3 hours. The affinity chromatography gel was washed sequentially with aqueous methanol (50%, 60 ml), water (60 ml) and application buffer (60 ml) and stored at 4° C. until required.

Examples 11–18

Preparation of affinity chromatography matrices

Each of the dipeptide derivatives prepared as described in Examples 2 to 9 was coupled to a gel matrix in a manner analogous to that described in Example 10 to give the affinity chromatography gels of Examples 11 to 18 respectively.

Example 19

Affinity chromatography

Spray-dried papaya latex (0.03 g of protein) obtained from Powell & Scholefield, UK in "application" buffer (Sodium phosphate (50 mM); EDTA (1 mM); ethanediol (33%), pH 6.8) plus dithiothreitol (2 mM) or cysteine (4 mM) (1.5 ml) was applied to a 1 ml column of each of the affinity chromatography matrices of Examples 10–18. At least one of five different eluents was used as follows:

Eluent A=Hydroxyethyldisulphide (100 mM) in aqueous ethanediol (33%) containing sodium citrate (50 mM) and EDTA (1 mM), pH 4.5; column equilibrated overnight before elution.

Eluent B=2,2'-Dipyridyldisulphide (30 mM) in aqueous ethanediol (33%) containing sodium citrate (50 mM) and EDTA (1 mM), pH 4.5; column equilibrated overnight before elution.

Eluent C=Methylpyridyldisulphide (30 mM) in aqeuous ethanediol (33%) containing sodium citrate (50 mM) and EDTA (mM), pH 4.5; column equilibrated overnight before elution.

Eluent D=Mersalyl acid (10 mM) in aqueous ethanediol (33%) containing sodium hydroxide (50 mM) and EDTA (25 mM), adjusted to pH 4.5 with acetic acid; continuous elution.

Eluent E=HgCl$_2$ (10 mM) in aqueous ethanediol (33%) containing sodium acetate (50 mM), pH 4.5; continuous elution.

Elution with each eluent was assessed by inspection of the A$_{280}$ trace of the eluted material after standard Mono S (Pharmacia) chromatography. The results are summarised in Table 1 below:

TABLE 1

| Binding and Elution of Chymopapain | | | | | | |
|---|---|---|---|---|---|---|
| Inhibitory | Matrix | Eluent | | | | |
| Peptide | (Example No.) | A | B | C | D | E |
| L-Ala-L-PheSc | 10 | − | ND | + | + | + |
| L-Phe-L-PheSc | 11 | − | + | + | + | + |
| L-Phe-L-PheMo | 12 | − | + | ND | ND | ND |
| L-Phe-D-PheSc | 13 | − | ND | + | + | + |
| L-Phe-L-PheOx | 14 | + | + | ND | ND | ND |
| L-Ala-D-PheSc | 15 | + | ND | ND | + | ND |
| L-Tyr-L-PheSc | 16 | + | ND | ND | + | ND |
| L-Ala-L-ChaSe | 17 | + | ND | ND | ND | + |
| L-Ala-L-LeuSc | 18 | + | ND | ND | ND | + |

+ Chymopapain bound and eluted
− Chymopapain not bound and/or not eluted
ND Not determined Example 20

Purification of chymopapain (i) Commercial spray dried latex of *Carica papaya* (1 g) obtained from Powell & Scholefield, UK was stirred for 1 hour with distilled water (5 ml) and the undissolved material removed by centrifugation at 9000×g for 30 minutes at 4° C. The pellet was discarded and the pH of the supernatant was adjusted to pH 1.8 with hydrochloric acid (1M) over a period of 20 minutes. Stirring was continued at 4° C. for 60 minutes and the pH was re-adjusted to pH 1.8 if required.

(ii) The mixture was centrifuged at 9000×g for 30 minutes at 4° C. and the pellet was discarded.

(iii) (a) The pH of the supernatant was adjusted to pH 6.8 by dropwise addition of NaOH (5M) over a period of 10 minutes. A purple-blue colouration was noted to appear in the solution.

(b) The resultant purple-blue solution was dialysed extensively against 10 volumes of "application" buffer (sodium phosphate (50 mM; EDTA (1 mM); ethanediol (33%), pH 6.8) with three buffer changes. The dialysant was centrifuged at 4000×g for 10 minutes and the protein content of the decanted supernatant containing chymopapain was adjusted to approximately 30 mg/ml. The chymopapain solution was activated by the addition of cysteine to a final concentration of 4 mM and left to stand for 15 minutes at 0° C.

(iv) The activated chymopapain solution was applied to an 8 ml column of ECH-Sepharose$^R$ coupled to L-Ala-L-PheSc (prepared as described in Example 10), previously equilibrated with application buffer, at a flow rate of 36 ml/cm$^2$/hour. The column was washed sequentially with application buffer (2 bed vol.), aqueous sodium citrate (50 mM) in ethanediol (33%), pH 4.5 (2 bed vol.) and aqueous sodium acetate (50 mM); EDTA (25 mM); mersalyl (10 mM) in ethanediol (33%), pH 4.5 (2 bed vol.) and then incubated at room temperature for 2 hours.

(v) Chymopapain was eluted with aqueous sodium acetate (50 mM) containing mersalyl (10 mM) (3 bed vol.) and fractions (4 ml) were collected. The enzyme activity of the eluted fractions was assayed for specific activity against BAPNA as hereinbefore described.

Active fractions were pooled and further purified by cation-exchange chromatography on a Mono-S HR$^R$ 10/10 (Pharmacia) column with a "starting" phosphate buffer of Na$^+$ (50 mM); EDTA (1 mM); NaN$_3$ (0.01%), pH 7.2 and a "limiting" phosphate buffer of Na$^+$ (800 mM); EDTA (1 mM); NaN$_3$ (0.0%), pH 7.2. Elution was carried out with a salt gradient of 2.7 mM/ml and a flow rate of 2 ml/min. Fractions (4 ml) were collected, protein concentrations estimated by measuring absorbance at 280 nm and enzyme activity assayed by BAPNA hydrolysis.

The chymopapain-containing fractions were pooled and dialysed extensively against distilled and deionised water or aqueous EDTA (1 mM) and freeze-dried for storage.

Example 21

Purification of chymopapain-BAPNA assay results (i) Commercial spray-dried latex of *Carica papaya* (1 g) obtained from Powell & Scholefield, UK, was stirred in water (5 ml) for 60 minutes at 20° C. Insoluble material was removed by centrifugation at 9000×g for 30 minutes at 4° C. The pellet was discarded and the pH of the supernatant was adjusted to pH 1.8 by the dropwise addition of hydrochloric acid (1M) over a period of 20 minutes. The mixture was stirred for 15 minutes at 4° C. and after 5 minutes the pH was checked and adjusted if necessary.

(ii) The precipitate was removed by centrifugation at 9000×g for 30 minutes at 4° C.

(iii) (a) The supernatant was adjusted to pH 7.0 by dropwise addition with stirring of aqueous sodium hydroxide (5M). The precipitate was removed by centrifugation at 9000×g for 30 minutes at 4° C.

(b) The resulting supernatant was applied to a Mono S HR 10/10 (Pharmacia) cation-exchange column, which had been pre-equilibrated with aqueous $Na_2HPO_4/NaH_2PO_4$ (50 mM $Na^+$) containing EDTA (1 mM), pH 7.2 (buffer A). Following sample application, the column was washed (2 ml/min) with buffer A until the $A_{280}$ returned to zero. A gradient (2.7 mM $Na^+$/ml) to $Na_2HPO_4/NaH_2PO_4$ (0.80M $Na^+$) was then applied to the column and 4 ml fractions were collected. The fractions were assayed for activity against BAPNA. The large chymopapain peak, determined immunologically, eluted between 0.17–0.28M $Na^+$. Fractions active against BAPNA in this region were pooled and ethanediol was added to 33% (v/v). All other fractions, including those active against BAPNA in the later-eluting (0.47–0.59M $Na^+$) papaya proteinase III peak, were discarded.

(iv) A column (15 ml bed vol. ) of ECH-Sepharose$^R$ coupled to L-Ala-L-PheSc (prepared as described in Example 10) was washed (39 ml/hr/cm$^2$) with aqueous $NaH_2PO_4/Na_2HPO_4$ (50 mM $Na^{30}$ ) containing EDTA (1 mM) in ethanediol (33% v/v), pH 6.8 (application buffer). The chymopapain pool (above) was activated by the addition of cysteine base (4 mM final concentration) and left for 15 minutes at 0° C. It was then applied to the column, followed by 60 ml of application buffer.

(v) Sodium acetate (50 mM) buffer, pH 4.5, containing $HgCl_2$ (10 mM, 45 ml) was then applied. 5 ml Fractions were collected throughout. The fractions were assayed for activity against BAPNA.

Fractions containing the peak of activity which was retarded by the column and eluted by the $HgCl_2$— containing buffer were pooled and re-applied to the Mono S column. The column was washed with buffer A and then 7 bed vol. of buffer A containing cysteine base (4 mM) was applied to the column. The flow was stopped for 30 minutes to allow mercury to be displaced from the enzyme. The flow was then resumed and the column washed again with buffer A before the application of a gradient up to $NaH_2PO_4/Na_2HPO_4$ (0.80M $Na^+$) as described above. Fractions active against BAPNA were combined, cysteine base added (4 mM final concentration) and the pool then left at 0° C. for 15 minutes.

Chelex resin (Bio-Rad, UK; 0.5 g) was packed into a column and washed with buffer A. The pool containing chymopapain was passed through the Chelex column, then extensively dialysed into aqueous EDTA (1 mM) and freeze-dried.

The progress of the purification of chymopapain is summarised in Table 2.

TABLE 2

Purification of Chymopapain

| | Protein (mg) | BAPNA Activity* (units) | BAPNA Specific Activity* (units mg$^{-1}$) | Yield +/ (%) | Purification (fold) |
| --- | --- | --- | --- | --- | --- |
| Spray-dried latex | 441 | 493,712 | 1,120 | 100 | 1 |
| Acid Treatment | 361 | 238,636 | 661 | 48 | 0.59 |
| Cation-exchange chromatography | 58 | 133,748 | 2,306 | 27 | 2.06 |
| Sepharose-L-Ala-L-PheSc | 27.5 | 112,475 | 4,090 | 23 | 3.65 |
| Cation-exchange chromatography | 11 | 44,687 | 4,062 | 9 | 3.63 |
| Chelex | 10.5 | 43,301 | 4,124 | 9 | 3.68 |

+The yield given is the yield of activity against BAPNA (also a substrate for papain and papaya proteinase III)
*BAPNA Assay Method No. 2

Example 22

Preparation of chymopapain-specific IgG antibodies raised in rabbit

Pure chymopapain prepared as described in Example 21 was mildly carboxymethylated before use by the method described by Zucker et al (1985) loc. cit. The antiserum to chymopapain was raised in a rabbit by intramuscular injection of 360 µg of the carboxymethylated protein in Freund's complete adjuvant, followed after a fortnight by a subcutaneous injection of 100 µg in incomplete adjuvant. IgG was partially purified from the antisera by ammonium sulphate fractionation as described by Heide and Schwick (1978) loc. cit, followed by dialysis into aqueous sodium phosphate (10 mM) containing NaCl (0.14M), pH 7.3.

Example 23

Purification of chymopapain and immunological quantitation of chymopapain and PPIV (i–iii) Commercial spray-dried latex of *Carica papaya* (1 g) obtained from Powell & Scholefield, UK was prepared and subjected to pH 1.8 treatment as described in Example 21 (i–iiia).

(iv) A column (1 ml bed vol.) of ECH-Sepharose$^R$ coupled to L-Ala-L-PheSc (prepared as described in Example 10) was washed as described in Example 21 (iv). The final supernatant from the pH 1.8 treatment was dialysed into aqueous $NaH_2PO_4/Na_2HPO_4$ (50 mM $Na^+$) containing EDTA (1 mM) in ethanediol (33% v/v) pH 6.8 (application buffer), centrifuged at 4000×g for 10 minutes and the supernatant activated by the addition of dithiothreitol (2 mM final concentration) for 15 minutes at 20° C. It was then applied to the affinity column (39 ml/hr/cm$^2$) and was followed by 60 ml of application buffer. Sodium citrate buffer (50 mM), pH 4.5, containing EDTA (1 mM) and methylpyridyldisulphide (30 mM; 15 ml) [synthesised as described by Salih et al., Biochem. J. (1987), 247, 181–193] was applied to the column. The flow was stopped and the disulphide-containing buffer was left on the column overnight (18 hours) at 20° C.

(v) The flow was resumed with the addition of 45 ml of the same buffer containing methylpyridyldisulphide followed by 30 ml of application buffer. Fractions (5 ml) were collected throughout.

The fractions were assayed for activity against BAPNA. Fractions containing the peak of activity which was retarded by the column and eluted in the methylpyridyldisulphide-containing buffer were pooled and applied (40 ml/hr/cm$^2$) to a column (80 ml bed vol.) of Sephadex$^R$ LH-20 (Pharmacia) that had been equilibrated with aqueous EDTA (1 mM) in ethanediol (33% v/v). Chromatography was continued by the application of 300 ml of this buffer. Fractions (8 ml) were monitored by $\Delta A_{271}$ and as saved for activity against BAPNA.

The fractions comprising the peak of activity against BAPNA (which was followed by a further peak of $A_{271}$) were pooled and applied to a Mono S HR 10/10 cation-exchange column and run as described in Example 21 (iiib). Fractions active against BAPNA were combined.

Spray-dried latex and the material recovered from the pH 1.8 treatment, affinity chromatography and cation-exchange chromatography, were analysed for the presence of PPIV by single radial immunodiffusion as described hereinbefore. The same method was used for chymopapain quantitation, with a chymopapain mono-specific antibody raised in rabbit prepared as described in Example 22. The standard curve for chymopapain was generated by the use of chymopapain purified by methods described herein and shown to be free of both PPIV and PPIII by single radial immunodiffusion. The results are shown in Table 3.

TABLE 3

Purification of chymopapain and immunological quantitation of chymopapain and PPIV

| | Protein (mg) | BAPNA Specific Activity* (units mg$^{-1}$) | Chymo-papain (mg) | PPIV (% of total protein) |
|---|---|---|---|---|
| Spray-dried latex | 468 | 1,000 | 144 | 18.7 |
| Acid treatment | 157 | 1,433 | 92 | <0.1 |
| Sepharose-L-Ala-L-PheSC | 24 | 4,000 | 28 | † |
| Cation-exchange chromatography | 15 | 3,533 | 14 | † |

TABLE 3-continued

Purification of chymopapain and immunological quantitation of chymopapain and PPIV

| | Protein (mg) | BAPNA Specific Activity* (units mg$^{-1}$) | Chymo-papain (mg) | PPIV (% of total protein) |
|---|---|---|---|---|

†= not detected
*BAPNA Assay Method No. 2

Example 24

Chymopapain allergy study

Forty human serum samples were purchased from 3M Diagnostic Systems, USA. These samples had already undergone a commercially available test, known by the trade name Chymofast, for IgE against a commercially available form of chymopapain Chymodiactin$^R$. Twenty of the samples had been designated as Chymofast positive and twenty were negative. The forty samples were received "blind" and were further tested for naturally acquired IgE antibodies against Chymodiactin$^R$, PPIII, PPIV and against purified chymopapain (purified by methods described herein and shown to be free of both PPIV and PPIII by single radial immunodiffusion) using a modified solid phase enzyme-linked immunosorbent assay (ELISA) utilising the biotin-avidin system, as summarised below:

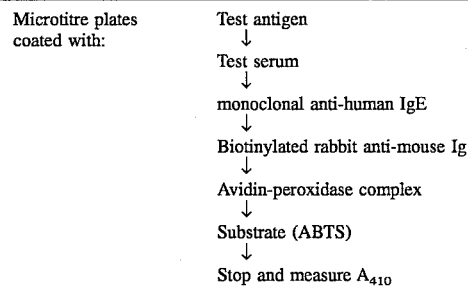

Chymodiactin$^R$ was used within the expiry date, PPIV was purified as described herein and PPIII was purified in accordance with Buttle and Barrett (1984), loc. cit. All antigens were inactivated by mild carboxymethylation with iodoacetic acid (10 mM) as described by Buttle and Barrett (1984), loc. cit., prior to use.

The wells of a microtitre plate were coated with test antigen by incubating each well with 100 μl test antigen (10 μg/ml) in sodium carbonate buffer (0.05M, pH 9.6). Donor horse serum (4%) was then used to reduce non-specific binding during subsequent steps. Incubation with test serum (1/20 dilution) in PBS (0.1% Tween, 2% horse serum, 10 mM EDTA, 50 μg/ml heparin; pH 7.2 (100 μl/well) at 37° C. for 4 hours was followed by monoclonal anti-human IgE (prepared as described by Kemeny & Richards in J. Immunol. Methods (1988), 108, 105-1 μg/ml, 100 l/well) at 37° C. for 3 hours and the biotinylated rabbit anti-mouse immunoglobulin (available from Dakopatts, Denmark-1 μg/ml, 100 μl/well) at room temperature overnight. The wells were incubated for 30 minutes at 37° C. with avidin-peroxidase (10 μl/ml, 100 μl/well), substrate [2,2'-azinobis(3-ethylbenzthiazoline sulphonic acid), ABTS, 0.5 mg/ml] in buffer (100 mM citric acid, 200 mM $Na_2HPO_4$, pH 4.2, activated with 1 μl/ml $H_2O_2$) added and the wells incubated at room temperature for 30 minutes. The reaction was stopped by addition of 100 μl/well 100 mM citric acid, 0.0% NaN$_3$ and the absorbance at 410 nm determined for each well using a Micro ELISA reader (Dynatech). IgE standards were assayed over the range 0.075 to 4.8 ng/ml (2.4 ng IgE=1 International Unit IgE). The Enzfitter programme (Leatherbarrow, R. J., 1985, Enzfitter for IBM PC, Elsevier-Biosoft, 68 Hills Road, Cambridge CB2 1LA, UK) was used to calculate the concentrations of IgE directed against each of the four antigen preparations, Chymodiactin$^R$, PPIII, PPIV and chymopapain prepared as described in Example 23.

26 of the 40 serum samples tested contained IgE antibodies against Chymodiactin$^R$ and the values obtained for PPIII, PPIV and chymopapain from the twelve most reactive against Chymodiactin$^R$ are shown in Table 4 below. The mean and standard error values were derived from nine determinations.

It can be seen that of these 12 serum samples containing anti-Chymodiactin antibodies, in only two did anti-chymopapain represent the major IgE response and antibodies against PPIII and PPIV accounted for approximately 75% of the relevant IgE detected.

the same volume of water to the other set. The tubes were then preincubated and assayed for azocasein hydrolysing activity.

The effect of chicken cystatin on the hydrolysis of azocasein by the enzyme mixtures was expressed as percentage inhibition of the activity produced by the same enzyme mixtures in the absence of cystatin as shown in Table 5.

TABLE 5

The percentage inhibition by chicken cystatin of mixtures of chymopapain and PPIV

| PPIV (nM) | Chymopapain (nM) | $A_{366}$ − cystatin | $A_{366}$ + cystatin | % Inhibition |
|---|---|---|---|---|
| 100 | 0 | 0.092 | 0.094 | 0 |
| 80 | 20 | 0.158 | 0.102 | 35.4 |
| 70 | 30 | 0.191 | 0.088 | 54.0 |
| 60 | 40 | 0.316 | 0.06 | 80.0 |
| 50 | 50 | 0.347 | 0.058 | 83.3 |
| 40 | 60 | 0.428 | 0.066 | 84.5 |
| 30 | 70 | 0.543 | 0.028 | 94.8 |
| 20 | 80 | 0.588 | 0.033 | 94.4 |
| 0 | 100 | 0.733 | 0.008 | 98.9 |

TABLE 4

Specific IgE concentrations (IU/ml) in serum samples containing IgE antibodies against Chymodiactin$^R$

| | PPIV | | PPIII | | Chymopapain | | | |
|---|---|---|---|---|---|---|---|---|
| Sample | Mean | SEM | Mean | SEM | Mean | SEM | Total | % Chymopapain |
| 1 | 19.9 | 1.7 | 18.8 | 1.7 | 8.2 | 1.3 | 46.9 | 18 |
| 2 | 5.1 | 0.3 | 4.0 | 0.1 | 3.2 | 0.4 | 12.3 | 26 |
| 3 | 5.9 | 0.4 | 2.7 | 0.3 | 1.2 | 0.3 | 9.8 | 12 |
| 4 | 1.8 | 0.1 | 2.3 | 0.2 | 1.7 | 0.1 | 5.8 | 29 |
| 5 | 3.4 | 0.2 | 2.0 | 0.2 | 1.6 | 0.3 | 7.0 | 23 |
| 6 | 3.1 | 0.2 | 0.3 | 0.01 | 0.3 | 0.03 | 3.7 | 8 |
| 7 | 2.6 | 0.2 | 1.6 | 0.2 | 0.9 | 0.2 | 5.1 | 18 |
| 8 | 2.0 | 0.1 | 1.1 | 0.1 | 1.3 | 0.2 | 4.4 | 30 |
| 9 | 1.5 | 0.2 | 0.3 | 0.07 | 1.7 | 0.2 | 3.5 | 49 |
| 10 | 1.0 | 0.1 | 0.3 | 0.09 | 0.5 | 0.1 | 1.8 | 28 |
| 11 | 3.6 | 0.4 | 1.4 | 0.2 | 0.7 | 0.07 | 5.7 | 12 |
| 12 | 0.6 | 0.1 | 0.4 | 0.09 | 2.3 | 0.2 | 3.3 | 70 |
| Total | 50.5 | | 35.2 | | 23.6 | | 109.3 | Ave. 22 |

Example 25

The inhibition by chicken cystatin of mixtures of chymopapain and PPIV

Chymopapain was purified as described in Example 23 and standardised by active-site titration with E-64, using BAPNA as substrate (Zucker et al., 1985, Biochem. Biophys. Acta 828, 196–204). PPIV, purified as described above, was also titrated with E-64, by an adaptation of this method for the use of azocasein as substrate.

Chicken cystatin form 2 was purified as described by Anastasi et al., 1983, Biochem. J. 211, 129–138 and standardised by titration with papain which had previously been titrated with E-64.

The assays for azocasein hydrolysis were done by the method of Rowan et al., 1988, loc. cit., except that a 15 minute, 40° C. preincubation of enzymes and inhibitor was incorporated prior to addition of substrate.

Two sets of 9 tubes were taken, and 125 μl of 0.40M sodium phosphate buffer containing 4 mM EDTA and 16 mM cysteine base, pH 6.8 was placed in each tube. Chymopapain and PPIV were added, in varying ratios to a final proteinase concentration of 100 nM. To one set of tubes chicken cystatin was added to 1 μM final concentration, and It can be seen that the degree of inhibition by chicken cystatin was inversely related to the concentration of PPIV.

Example 26

Purification of chymopapain by acid precipitation at pH 2.2–1.2 i) Commercial spray-dried latex of *Carica papaya* obtained from Powell & Scholefield, UK was made up to 20% (w/v) with distilled water and stirred for 1 hour. The undissolved material was removed by centrifugation at 9000×g for 30 minutes at 4° C. The pellet was discarded and the pH of the supernatant was reduced by the addition of hydrochloric acid (1M) dropwise with stirring at 4° C. at a rate of 40 μl/min/ml. The pH of the mixture was continuously monitored using a Radiometer combined electrode (Type GK 2401C) calibrated with pH 4.01 and pH 1.09 buffer standards (Radiometer, 25° C.). At pH 2.2, and at intervals of 0.2 pH units below this down to pH 1.2, addition of acid was stopped and the pH was kept constant while stirring at 4° C. was continued. An aliquot (equivalent to 10 ml of the starting solution) was then removed and stored. The addition of acid to the remaining solution was continued until the next pH interval was attained.

ii) All samples were centrifuged at 9.000×g for 30 minutes at 4° C. and the pellets were discarded.

iii) The pH of each supernatant was adjusted to pH 6.8 by dropwise (400 μl/min) addition of NaOH (1M). Each sample was centrifuged again at 9000×g for 30 minutes to remove any additional precipitate.

In a further experiment acid precipitation at pH 1.8 was carried out at 25° C.

The final supernatants were each assayed for activity against BAPNA and for the presence of PPIV and chymopapain according to the invention by single radial immunodiffusion as described hereinbefore. The results are shown in Table 6 and indicate that removal of PPIV to levels of <0.1% of total protein was achieved by acid precipitation at 4° C. at pH 1.8 and below and to <0.5% by precipitation at 25° C. at pH 1.8.

TABLE 6

| Conditions | Temp. (°C.) | Protein (mg) | BAPNA Activity* (Units × $10^5$) | BAPNA Specific Activity* (Units $mg^{-1}$) | Chymopapain (mg) | PPIV (% of total protein) |
|---|---|---|---|---|---|---|
| Starting solution | — | 946 | 15.8 | 1670 | 208 | 20.30 |
| pH 2.2 | 4 | 848 | 9.5 | 1120 | 231 | 7.56 |
| pH 2.0 | 4 | 865 | 9.1 | 1052 | 230 | 1.20 |
| pH 1.8 | 4 | 796 | 9.0 | 1131 | 199 | 0.09 |
| pH 1.6 | 4 | 828 | 7.7 | 930 | 224 | 0.06 |
| pH 1.4 | 4 | 869 | 7.8 | 898 | 225 | 0.05 |
| pH 1.2 | 4 | 784 | 7.1 | 906 | 166 | 0.03 |
| pH 1.8 | 20 | 925 | 8.3 | 897 | 269 | 0.43 |

*BAPNA Assay Method No. 2

Example 27

Preparation of mono-specific IgG antibodies raised in sheep

Pure chymopapain prepared as described in Example 21 was mildly carboxymethylated before use by the method described by Zucker et al (1985) loc. cit. and dialysed into aqueous sodium phosphate (10 mM), pH 7.3 containing NaCl (0.14M). The antiserum to chymopapain was raised in a sheep by intramuscular injection of 100 μg of the carboxymethylated protein in Freund's complete adjuvant, followed after one month by 50 μg presented in the same way. IgG was partially purified from the antisera by ammonium sulphate fractionation as described by Heide and Schwick (1978) loc. cit, followed by dialysis into aqueous sodium phosphate (10 mM) containing NaCl (0.14M), pH 7.3.

IgG preparations of antibodies against papain, papaya proteinase III and papaya proteinase IV were prepared in a similar manner.

The individual carboxymethylated antigens were separately coupled in accordance with the manufacturers instructions to columns supplied under the trade name Zetaffinity (Anachem) equilibrated in aqueous sodium phosphate (10 mM), pH 7.3 containing NaCl (0.14M). Potentially contaminating or cross-reacting antibodies were absorbed out of the IgG preparations by passage through these columns so that the final IgG preparations gave precipitin reactions with their respective antigens but no precipitating cross-reaction with the different antigens. The antigen-linked columns were regenerated for re-use with aqueous diethylamine (0.05M), pH 11.5 and promptly re-equilibrated in phosphate buffer.

In this way mono-specific preparations of IgG antibodies against chymopapain, PPIII, PPIV and papain were prepared which could be used for quantitative assays of each antigen by single radial immunodiffusion as described hereinbefore.

Example 28

Purification of chymopapain-acid precipitation at pH 1.5 i) Commercial spray-dried latex of Carica papaya (20 g) obtained from Siebels, USA, was stirred in deionised and distilled water (pre-cooled to 4° C., 250 ml) for 60 minutes at 0° C. The pH of the mixture was adjusted to pH 1.5 by the addition of HCl (1N) at a rate of 10 μl/min/ml during continuous pH monitoring using a Radiometer combined electrode (Type GK 2401C) calibrated with pH 4.01 and 1.09 buffer standards (Radiometer, 25° C.). When pH 1.5 was attained, a period of 10 minutes was allowed for the pH to stabilize during which time the pH was further adjusted if necessary.

ii) The mixture was centrifuged at 12000×g for 30 minutes at 4° C. and the pellet was discarded.

iii) (a) The pH of the supernatant was adjusted to pH 7.0 by the addition of NaOH (1M) at a rate of 10 μl/min/ml during continuous pH monitoring using the Radiometer electrode calibrated with pH 7.01 buffer standard (Radiometer, 25° C). When pH 7.0 was attained, a period of 10 minutes was allowed for the pH to stabilize during which time the pH was further adjusted if necessary. The mixture was centrifuged at 12000×g for 30 minutes at 4° C. and the pellet was discarded.

(b) The supernatant was dialysed extensively at 4° C. against 30 volumes of deionised and distilled water with two changes made at 12 hour intervals.

The dialysed solution was further purified by cation-exchange chromatography on an S-Sepharose High Performance 35/100 column (Pharmacia). A maximum of 3 g protein (determined by $A_{280}$) was used for each run. The column was pre-equilibrated with aqueous EDTA (1 mM) at 4° C. Following sample application the column was washed with aqueous EDTA (1 mM) at 10 ml/min until the $A_{280}$ had returned to zero.

A gradient (0.175 mM $K^+$/ml) to 0.5M $K^+$ was applied to the column and 25 ml fractions were collected throughout. Peak fractions were assayed for activity against BAPNA.

The fractions containing chymopapain with the highest specific activity against BAPNA (eluted between 0.17 and 0.22M $K^+$) were pooled. The pooled chymopapain was extensively dialysed at 4° C. against 30 volumes of deionised and distilled water with five changes made at 12 hour intervals. The dialysate was freeze-dried and stored at −20° C.

The entire purification procedure was repeated on a number of occasions. The presence of chymopapain according to the invention, papain, PPIII and PPIV was assayed using single radial immunodiffusion as described hereinbefore and antibodies raised in sheep as described in Example 27. The activity against BAPNA and active site titration with iodoacetic acid was assessed using BAPNA Method No. 1 described hereinbefore. The progress of the purifications is summarised by the mean values shown in Table 7.

aqueous $HgCl_2$ (10 mM) in ethanediol (33% v/v) containing sodium acetate (50 mM), pH 4.5 and 25 ml fractions collected. Fractions containing activity against BAPNA were pooled and further purified by cation-exchange chromatography on an S-Sepharose High Performance 35/100 column (Pharmacia).

The column was pre-equilibrated with aqueous EDTA (1 mM) at 4° C. Following sample application the column was washed with aqueous EDTA (1 mM) at 10 ml/min until the $A_{280}$ had returned to zero. Three bed volumes of aqueous $K_2HPO_4/KH_2PO_4$ (50 mM $K^+$), pH 7.2 containing EDTA (1 mM) and L-cysteine (500 mM) were applied to the column and flow stopped for 30 minutes. A further three bed volumes of freshly prepared cysteine buffer was applied to the column and flow stopped for 30 minutes. The column was washed with a further six bed volumes of cysteine buffer and then re-equilibrated with aqueous $K_2HPO_4/KH_2PO_4$ (50 mM $K^+$) containing EDTA (1 mM), pH 7.2.

A gradient (0.175 mM $K^+$/ml) to 0.5M $K^+$ was applied to the column and 25 ml fractions were collected throughout.

TABLE 7

|  | Total protein (mg) | BAPNA Specific Activity (units mg$^{-1}$) | Active sites (%) | Chymopapain (% of total protein) | PPIV (% of total protein) | PPIII (% of total protein) | Papain (% of total protein) |
|---|---|---|---|---|---|---|---|
| Starting material | 10203 | 572 | 30 | 25 | 22 | 14 | 5 |
| pH 1.5 | 8168 | 461 | 28 | 30 | 0.1 | 14 | <0.1 |
| Dialysis | 4351 | 674 | 42 | 59 | 0.1 | 24 | <0.1 |
| Cation exchange chromatography | 948 | 1079 | 72 | 100 | 0.1 | <0.1 | <0.1 |
| Dialysis | 767 | 1098 | 89 | 100 | 0.1 | <0.1 | 0.1 |
| Freeze-dried | ND | 905 +  | ND | ND | ND | ND | ND |

ND Not Determined
+Protein estimated by total dry weight

Example 29

Purification of chymopapain-acid precipitation at pH 1.5 and affinity chromatography i–iii) Commercial spray-dried latex of Carica papaya (50 g) obtained from Siebels, USA, was prepared and subjected to pH 1.5 treatment as described in Example 28 (i–iiia). The supernatant was dialysed extensively at 4° C. against 30 volumes of deionised and distilled water with two changes made at 12 hour intervals.

iv) A column (350 ml bed volume) of ECH-Sepharose$^R$ coupled to L-Ala-L-PheSC (prepared as described in Example 10) was equilibrated with aqueous ethanediol (33% v/v) containing sodium acetate (50 mM), pH 4.5 overnight and then equilibrated with aqueous $NaH_2PO_4/Na_2HPO_4$ (50 mM $Na^+$) containing EDTA (1 mM) in ethanediol (33% v/v) pH 6.8 (application buffer).

The dialysed supernatant (above) was filtered using a 0.2 μm pore size filter and ethanediol added to 33%, (v/v). The pH of the solution was checked and adjusted to pH 7.0 if necessary. Freshly prepared aqueous L-cysteine (200 mM) was added to a concentration of 4 mM, the solution mixed well and allowed to stand for 15 minutes at 4° C. It was then applied to the affinity column at 4° C. at a flow rate of up to 40 ml/hr/cm$^2$. The column was washed with 10 bed volumes of application buffer.

v) Chymopapain was eluted with 3 bed volumes of

Peak fractions were assayed for activity against BAPNA. The first peak, eluted between 0.2 to 0.25M $K^+$, was chymopapain. The second peak, eluted at about 0.45M $K^+$, was papaya proteinase III.

The fractions containing chymopapain with the highest specific activity against BAPNA were pooled. The pooled chymopapain was extensively dialysed at 4° C. against 30 volumes of deionised and distilled water with five changes of water made at 12 hour intervals.

The chymopapain eluted from the cation-exchange column had been activated by the cysteine buffer and was therefore susceptible to inactivation by oxidation. In order to substantially prevent or reduce inactivation of the active enzyme by oxidation, fractions were collected into tubes containing a suspension of sodium tetrathionate (200 mM) to give a final concentration of 5 mM $NaS_4O_6$ in each fraction. Alternatively, the pooled chymopapain was dialysed under nitrogen against water which had been purged of oxygen by bubbling with nitrogen at a rate of 0.1 l/min for 30 minutes in a container sealed under nitrogen.

Finally the dialysate was freeze-dried and stored at −20° C.

The entire purification procedure was repeated on a number of occasions and the progress of the purifications (assayed as described in Example 28) is summarised by the mean values shown in Table 8.

TABLE 8

|  | Total protein (mg) | BAPNA Specific Activity (units mg$^{-1}$) | Active sites (%) | Chymopapain (% of total protein) | PPIV (% of total protein) | PPIII (% of total protein) | Papain (% of total protein) |
|---|---|---|---|---|---|---|---|
| Starting material | 25508 | 572 | 30 | 25 | 22 | 14 | 5 |
| pH 1.5 | 20421 | 401 | 28 | 30 | <0.1 | 14 | <0.1 |
| Dialysis | 10877 | 674 | 42 | 59 | <0.1 | 24 | <0.1 |
| Sepharose-L-Ala-L-PheSc | 1673 | 1446 | 86 | 66 | <0.1 | 13 | <0.1 |
| Cation exchange chromatography | 951 | 1625 | 100 | 100 | <0.1 | <0.1 | <0.1 |
| Dialysis | 828 | 1743 | 100 | ND | ND | ND | ND |
| Freeze-dried | ND | 1320+ | ND | ND | ND | ND | ND |

ND Not Determined
+Protein estimated by total dry weight

Example 30

Purification of chymopapain-acid precipitation at pH 1.5 and affinity chromatography i–iii) Commercial spray-dried latex of *Carica papaya* obtained from Siebels, USA, was prepared and subjected to pH 1.5 treatment, dialysis and cation-exchange chromatography on S-Sepharose$^R$ as described in Example 28.

iv) The fractions containing chymopapain with the highest specific activity against BAPNA were pooled and ethanediol added to 33% (v/v). Freshly prepared aqueous L-cysteine (200 mM) was added to a concentration of 4 mM and the solution applied to a column of ECH-Sepharose$^R$ coupled to L-Ala-L-PheSC as described in Example 29 (iv).

v) Chymopapain was eluted with 3 bed volumes of aqueous HgCl$_2$ (10 mM) in ethanediol (33% v/v) containing sodium acetate (50 mM), pH 4.5 and 25 ml fractions collected. Fractions containing activity against BAPNA were pooled and dialysed extensively at 4° C. against 30 volumes of deionised and distilled water with five changes made at 12 hour intervals. The dialysate was freeze-dried and stored at −20° C.

The progress of the purification (assayed as described in Example 28) is summarised in Table 9.

TABLE 9

|  | Total protein (mg) | BAPNA Specific Activity (units mg$^{-1}$) | Active sites (%) | Chymopapain (% of total protein) | PPIV (% of total protein) | PPIII (% of total protein) | Papain (% of total protein) |
|---|---|---|---|---|---|---|---|
| Starting material | 28795 | 632 | 31 | 27 | 25 | 16 | 6 |
| pH 1.5 | 23257 | 458 | 24 | 28 | <0.1 | 13 | <0.1 |
| Dialysis | 8319 | 916 | 57 | 75 | 0.2 | 25 | <0.1 |
| Cation exchange chromatography | 3102 | 1103 | 72 | 91 | <0.1 | <0.2 | <0.1 |
| Sepharose-L-Ala-L-PheSc | 947 | 1245 | 89 | ND | ND | ND | ND |
| Dialysis | 858 | 1587 | 88 | 100 | ND | <0.1 | <0.1 |
| Freeze-dried | 972 | 1265+ | 69 | ND | <0.1 | ND | ND |

ND Not Determined
+Protein estimated by total dry weight

Example 31

Two preparations of chymopapain according to the invention were assayed using BAPNA Assay Methods 1 and 2 on the same day. Protein was estimated by total dry weight. Chymopapain preparation A originated from a purification procedure as described in Example 28. Chymopapain preparation B originated from a purification procedure as described in Example 29 (final fractions collected in sodium tetrathionate). Results of assays carried out in triplicate were as shown in Table 10.

TABLE 10

| Chymopapain Preparation | BAPNA Specific Activity (Units mg$^{-1}$) | |
| --- | --- | --- |
| | Assay Method No. 1 | Assay Method No. 2 |
| A | 855 | 2227 |
| B | 1261 | 3591 |

Example 32

Chymopapain purified as described in Example 29 and dialysed under nitrogen as described therein was freeze-dried and stored at −20° C. The freeze-dried chymopapain had a specific activity against BAPNA (1 mM) at 37° C. and pH 6.0 of 1345 units per mg.

To prepare 100 vials of a composition comprising purified chymopapain, 43.75 g of bulk solution is made up as described below. The bulk solution is maintained at 4° to 12° C. throughout processing.

L-(+) cysteine hydrochloride monohydrate (166 mg) is added to about 30 g water for injection to provide a concentration of 22 mM in the final volume. The pH of the solution is adjusted to pH 5.0 to 5.5 with NaOH (1M) or HCl (0.1M). The cysteine solution is added to purified chymopapain (358 mg) to provide a concentration of 11000 units/ml in the final volume. The pH of the stirred solution is adjusted to pH 5.9 to 6.1 with NaOH (1M) or HCl (0.1M) and made up to 43.75 g with water for injection. The solution is sterilized by passing through two 0.2 micron pore size filters in series. 0.4 g aliquots of the solution is filled into 100×5 ml glass vials. The vials are stoppered, the water removed by freeze-drying under reduced pressure, and the vials containing lyophilised product are sealed under vacuum.

Each vial contains a white amorphous powder containing 3.27 mg of chymopapain and 1.52 mg of sodium cysteinate hydrochloride (nominally 4000 units and 8 μmoles respectively allowing for 10% overage). The compositions are generally reconstituted immediately prior to use by the addition of 2 ml water for injection to give an injectable solution nominally containing 4000 units of chymopapain and 4 mM L-cysteine.

We claim:

1. A composition comprising chymopapain which has a specific activity against 1mM of N-α-benzoyl-DL-arginine p-nitroanilide at 37° C. and pH 6.0 of between 800 and 1700 units per mg and which contains less than 0.2% each of papaya proteinase III (PPIII), papain and papaya proteinase IV (PPIV) in combination with a pharmaceutically acceptable carrier and a pharmaceutically acceptable reducing agent, wherein said reducing agent prevents inactivation of said chymopapain by oxidation.

2. The composition according to claim 1, wherein said specific activity is between 1000 and 1700 units per mg.

3. A composition as claimed in claim 1 sealed under anhydrous conditions in an evacuated vial or ampoule.

4. A pharmaceutical composition as claimed in claim 3 in unit dosage form for parenteral administration.

5. A composition comprising chymopapain which has a specific activity against 2.5 mM of N-α-benzoyl-DL-arginine p-nitroanilide at 40° C. and pH 6.8 of between 3000 and 4500 units per mg and which contains less than 0.2% each of papaya proteinase III (PPIII), papain and papaya proteinase IV (PPIV) in combination with a pharmaceutically acceptable carrier and a pharmaceutically acceptable reducing agent, wherein said reducing agent prevents inactivation of said chymopapain by oxidation.

6. The composition according to claim 5, wherein said specific activity is between 3500 and 4500 units per mg.

* * * * *

UNITED STATES PATENT AND TRADEMARK OFFICE
CERTIFICATE OF CORRECTION

PATENT NO. : 5,468,480
DATED : November 21, 1995
INVENTOR(S) : Barrett et al.

It is certified that error appears in the above-indentified patent and that said Letters Patent is hereby corrected as shown below:

Title page, item,

[30] include line 3 to read
　　Apr. 27, 1990 [GB]　PCT.......PCT/EP90/00647

Signed and Sealed this

Twentieth Day of February, 1996

Attest:

Attesting Officer

BRUCE LEHMAN

*Commissioner of Patents and Trademarks*